US008486902B2

(12) United States Patent
Rodgers et al.

(10) Patent No.: US 8,486,902 B2
(45) Date of Patent: *Jul. 16, 2013

(54) HYDROXYL, KETO, AND GLUCURONIDE DERIVATIVES OF 3-(4-(7H-PYRROLO[2,3-D]PYRIMIDIN-4-YL)-1H-PYRAZOL-1-YL)-3-CYCLOPENTYLPROPANENITRILE

(75) Inventors: James D. Rodgers, Landenberg, PA (US); Adam Shilling, Wilmington, DE (US); Argyrios G. Arvanitis, Kennett Square, PA (US); Stacey Shepard, Wilmington, DE (US); Laurine G. Galya, Wilmington, DE (US); Mei Li, Wilmington, DE (US); Frank M. Nedza, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 16 days.

This patent is subject to a terminal disclaimer.

(21) Appl. No.: 12/901,001

(22) Filed: Oct. 8, 2010

(65) Prior Publication Data

US 2011/0086810 A1   Apr. 14, 2011

Related U.S. Application Data

(60) Provisional application No. 61/250,387, filed on Oct. 9, 2009, provisional application No. 61/316,218, filed on Mar. 22, 2010.

(51) Int. Cl.
| | |
|---|---|
| C07H 17/02 | (2006.01) |
| C07D 487/04 | (2006.01) |
| A61K 31/70 | (2006.01) |
| A61K 31/519 | (2006.01) |
| A61P 37/06 | (2006.01) |
| A61P 35/00 | (2006.01) |
| A61P 25/28 | (2006.01) |
| A01N 43/04 | (2006.01) |

(52) U.S. Cl.
USPC ........... 514/35; 514/27; 514/265.1; 536/17.4; 536/18.1; 544/265; 544/180

(58) Field of Classification Search
None
See application file for complete search history.

(56) References Cited

U.S. PATENT DOCUMENTS

| | | | |
|---|---|---|---|
| 7,598,257 B2 | 10/2009 | Rodgers et al. | |
| 7,834,022 B2 * | 11/2010 | Rodgers et al. | ............ 514/265.1 |
| 8,158,616 B2 | 4/2012 | Rodgers et al. | |
| 2007/0135461 A1 | 6/2007 | Rodgers et al. | |
| 2008/0312258 A1 | 12/2008 | Rodgers et al. | |
| 2008/0312259 A1 | 12/2008 | Rodgers et al. | |
| 2009/0181959 A1 | 7/2009 | Rodgers et al. | |
| 2009/0233903 A1 | 9/2009 | Rodgers et al. | |
| 2010/0190981 A1 | 7/2010 | Zhou et al. | |
| 2010/0298334 A1 | 11/2010 | Rodgers et al. | |
| 2011/0059951 A1 | 3/2011 | Rodgers et al. | |
| 2011/0082159 A1 | 4/2011 | Rodgers et al. | |
| 2011/0207754 A1 | 8/2011 | Li et al. | |

FOREIGN PATENT DOCUMENTS

| | | |
|---|---|---|
| WO | 01/42246 A | 6/2001 |
| WO | 2006/096270 A | 9/2006 |
| WO | 2007/070514 A | 6/2007 |
| WO | 2007/117494 A | 10/2007 |

OTHER PUBLICATIONS

International Search Report dated Dec. 23, 2008, PCT Publication No. WO2008/157207.
International Search Report dated Nov. 11, 2010, PCT Publication No. WO2011/044481 (PCT/US2010/052011).
Written Opinion of the International Searching Authority dated Apr. 11, 2012, PCT Publication No. WO2011/044481 (PCT/US2010/052011).
Quiyan Lin, David Meloni, Yongchun Pan et al. "Enantioselective synthesis of Janus kinase inhibitor INCB018424 via an organocatalytic aza-Michael reaction" Organic Letters, vol. 11, No. 9, Mar. 27, 2009, pp. 1999-2002, XP002609063.

* cited by examiner

*Primary Examiner* — Traviss C McIntosh, III
(74) *Attorney, Agent, or Firm* — Lathrop & Gage LLP; Brian C. Trinque

(57) ABSTRACT

The present invention provides hydroxyl, keto, and glucuronide derivatives of 3-(4-(7H-pyrrolo[2,3-d]pyrimidin-4-yl)-1H-pyrazol-1-yl)-3-cyclopentylpropanenitrile.

14 Claims, No Drawings

HYDROXYL, KETO, AND GLUCURONIDE DERIVATIVES OF 3-(4-(7H-PYRROLO[2,3-D]PYRIMIDIN-4-YL)-1H-PYRAZOL-1-YL)-3-CYCLOPENTYLPROPANENITRILE

RELATED APPLICATIONS

This application claims priority to U.S. Provisional Application No. 61/250,387, filed Oct. 9, 2009, and U.S. Provisional Application No. 61/316,218, filed Mar. 22, 2010. The disclosure of these documents are incorporated herein by reference in their entirety.

FIELD OF THE INVENTION

The present invention provides hydroxyl, keto, and glucuronide derivatives of 3-(4-(7H-pyrrolo[2,3-d]pyrimidin-4-yl)-1H-pyrazol-1-yl)-3-cyclopentylpropanenitrile.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

The Janus Kinase (JAK) family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra).

Blocking signal transduction at the level of the JAK kinases holds promise for developing treatments for human cancers. Inhibition of the JAK kinases is also envisioned to have therapeutic benefits in patients suffering from skin immune disorders such as psoriasis, and skin sensitization. Accordingly, inhibitors of Janus kinases or related kinases are widely sought and several publications report effective classes of compounds. For example, certain JAK inhibitors, including (R)-3-(4-(7H-pyrrolo[2,3-d]pyrimidin-4-yl)-1H-pyrazol-1-yl)-3-cyclopentylpropanenitrile shown below, are reported in U.S. Ser. No. 11/637,545 (US 2007/0135461), filed Dec. 12, 2006; U.S. Ser. No. 12/138,082 (US 2009/0181959), filed Jul. 16, 2009; and certain metabolites of Compound I are reported in U.S. Ser. No. 12/137,883 (US 2008/0312258), filed Jun. 12, 2008, each of which is incorporated herein by reference in its entirety.

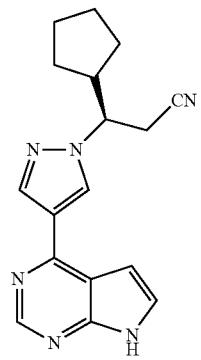

Thus, new or improved agents which inhibit kinases such as Janus kinases are continually needed for developing new and more effective pharmaceuticals to treat cancer and other diseases. The metabolites, compositions and methods described herein are directed toward these needs and other ends.

SUMMARY OF THE INVENTION

The present invention provides, inter alia, hydroxyl, keto, and glucuronide derivatives of a compound of Formula I:

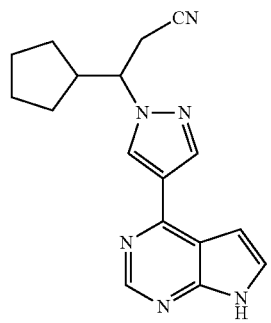

or a pharmaceutically acceptable salt thereof.

Thus, in one aspect, provided herein is a compound of Formula I:

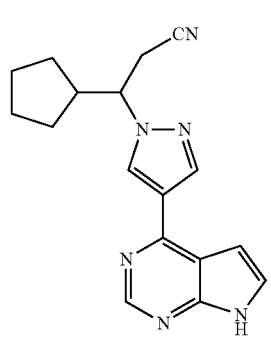

or a pharmaceutically acceptable salt thereof, wherein:

n C—H groups are each independently replaced with C—OH; or, one CH₂ group is independently replaced with a C=O; or, one C—H group is replaced with:

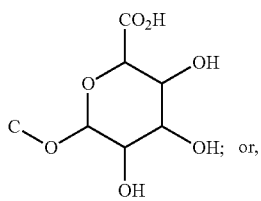

two C—H groups are each independently replaced with C—OH and one C—H group is replaced with:

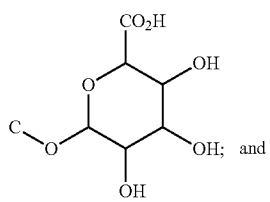

n is 1, 2, 3, or 4;
provided that the compound is not selected from:
3-(4-(7H-pyrrolo[2,3-d]pyrimidin-4-yl)-1H-pyrazol-1-yl)-3-(3-hydroxycyclopentyl)propanenitrile;
3-(4-(7H-pyrrolo[2,3-d]pyrimidin-4-yl)-1H-pyrazol-1-yl)-3-(2-hydroxycyclopentyl)propanenitrile;
3-(4-(7H-pyrrolo[2,3-d]pyrimidin-4-yl)-1H-pyrazol-1-yl)-3-(3-oxocyclopentyl)propanenitrile;
and pharmaceutically acceptable salts thereof.

In one embodiment of Formula I,
the carbon atom alpha to the cyano group is not replaced with a C—OH or C=P group; and
the carbon atom beta to the cyano group is not replaced with a C—OH group.

In another embodiment of the compound, n C—H groups are each independently replaced with C—OH. In another embodiment, n is 1. In yet another embodiment, n is 2. I still another embodiment, n is 3. In another embodiment, n is 4.
In another embodiment of Formula I, one CH₂ group is independently replaced with a C=O. In still another embodiment, one C—H group is replaced with

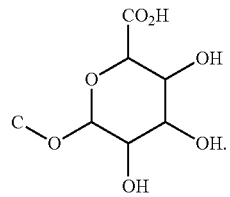

In another embodiment, one saturated C—H group is replaced with

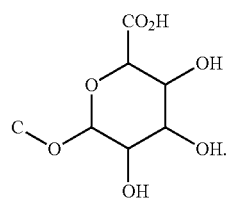

In yet another embodiment, two C—H groups are each independently replaced with C—OH and one C—H group is replaced with:

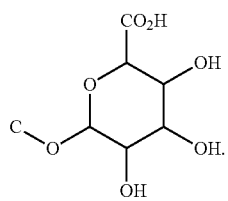

The present invention further provides compositions comprising compounds described herein, or a pharmaceutically acceptable salt thereof, and at least one pharmaceutically acceptable carrier.

The present invention further provides methods of modulating an activity of JAK comprising contacting JAK with certain compounds described herein, or pharmaceutically acceptable salt thereof. The present invention further provides methods of treating a disease in a patient, comprising administering to the patient a therapeutically effective amount of certain compounds described herein, or pharmaceutically acceptable salt thereof. In a particular embodiment, the disease is associated with JAK activity. Such diseases include, for example, allograft rejection or graft versus host disease. The disease can also be an autoimmune disease, including, but not limited to, a skin disorder, multiple sclerosis, rheumatoid arthritis, juvenile arthritis, type I diabetes, lupus, inflammatory bowel disease, Crohn's disease, myasthenia gravis, immunoglobulin nephropathies, myocarditis, or autoimmune thyroid disorder. The autoimmune disease can also be bullous skin disorder, e.g., pemphigus vulgaris (PV) or bullous pemphigoid (BP). The skin disorder can be atopic dermatitis, psoriasis, skin sensitization, skin irritation, skin rash, contact dermatitis or allergic contact sensitization.

In another embodiment, the disease is a viral disease. Examples of viral diseases that can be treated by the compounds described herein include Epstein Barr Virus (EBV), Hepatitis B, Hepatitis C, HIV, HTLV 1, Varicell-Zoster Virus (VZV) or Human Papilloma Virus (HPV).

In another embodiment, the disease is cancer, e.g., a solid tumor. The cancer to be treated can be prostate cancer, renal cancer, hepatic cancer, breast cancer, lung cancer, thyroid cancer, Kaposi's sarcoma, Castleman's disease or pancreatic cancer. In a particular embodiment, the cancer is prostate cancer. The cancer can be hematological. The cancer can also be a lymphoma, leukemia, or multiple myeloma. In another embodiment, the cancer is a skin cancer, e.g., cutaneous T-cell lymphoma or cutaneous B-cell lymphoma. In another embodiment, the cancer is multiple myeloma. The disease to be treated can also be fatigue resulting from or associated with cancer, or anorexia or cachexia resulting from or associated with cancer.

In another embodiment, the disease to be treated is a myeloproliferative disorder, e.g., polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), or systemic mast cell disease (SMCD).

In another embodiment, the disease to be treated is an inflammatory disease. The inflammatory disease can be an inflammatory disease of the eye, e.g., iritis, uveitis, scleritis, or conjunctivitis. The inflammatory disease can be an inflammatory disease of the respiratory tract, e.g., the upper respiratory tract or the lower respiratory tract. The inflammatory disease can be an inflammatory myopathy or myocarditis.

In another embodiment, the disease is ischemia reperfusion or related to an ischemic event.

DETAILED DESCRIPTION

The present invention provides, inter alia, hydroxyl, keto, and glucuronide derivatives of 3-(4-(7H-pyrrolo[2,3-d]pyrimidin-4-yl)-1H-pyrazol-1-yl)-3-cyclopentylpropanenitrile. In some embodiments, the compound is a metabolite of compound I. In some embodiments, the compound is an active metabolite which may modulate the activity of one or more JAKs and may be useful, for example, in the treatment of diseases associated with JAK expression or activity. In some embodiments, the level of a metabolite compound described herein is measured and profiled in order to aid a practitioner in the adjustment of dosage levels of the compound of Formula I.

Accordingly, the present invention provides a compound of Formula I:

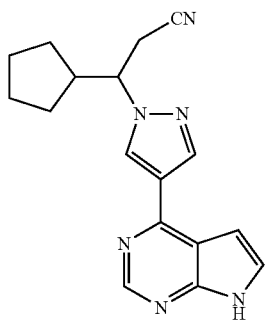

I or a pharmaceutically acceptable salt thereof, wherein:
n C—H groups are each independently replaced with C—OH; or,
one CH$_2$ group is independently replaced with a C=O; or,
one C—H group is replaced with:

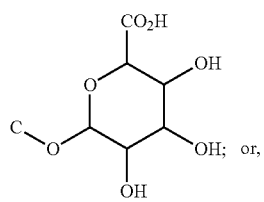

two C—H groups are each independently replaced with C—OH and one C—H group is replaced with:

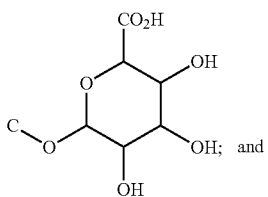

n is 1, 2, 3, or 4;
provided that the compound is not selected from:
3-(4-(7H-pyrrolo[2,3-d]pyrimidin-4-yl)-1H-pyrazol-1-yl)-3-(3-hydroxycyclopentyl)propanenitrile;
3-(4-(7H-pyrrolo[2,3-d]pyrimidin-4-yl)-1H-pyrazol-1-yl)-3-(2-hydroxycyclopentyl)propanenitrile;
3-(4-(7H-pyrrolo[2,3-d]pyrimidin-4-yl)-1H-pyrazol-1-yl)-3-(3-oxocyclopentyl)propanenitrile;
and pharmaceutically acceptable salts thereof.

In some embodiments, n C—H groups are each independently replaced with C—OH. In some embodiments, n is 1. In some embodiments, n is 2. In some embodiments, n is 3. In some embodiments, n is 4.

In some embodiments, one CH$_2$ group is independently replaced with a C=O.

In some embodiments, one C—H group is replaced with

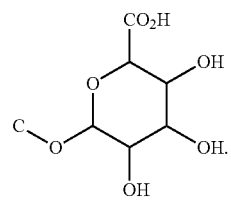

In some embodiments, one saturated C—H group is replaced with

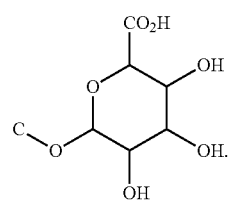

In some embodiments, two C—H groups are each independently replaced with C—OH and one C—H group is replaced with:

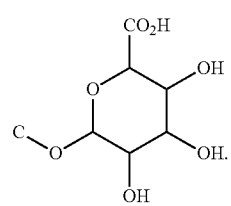

In some embodiments:
the carbon atom alpha to the cyano group is not replaced with a C—OH, C=O, or

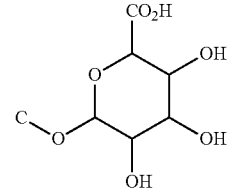

group; and
the carbon atom beta to the cyano group is not replaced with a C—OH or

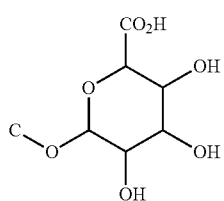

group.

In some embodiments:
the carbon atom alpha to the cyano group is not replaced with a C—OH or C=O group; and
the carbon atom beta to the cyano group is not replaced with a C—OH group.

In another embodiment, the present invention provides a compound of Formula II:

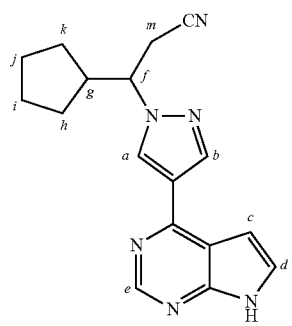

or a pharmaceutically acceptable salt thereof, wherein:
1, 2, 3, or 4 of carbons a, b, c, d, e, f, g, h, i, j, k or m are each independently substituted with OH; or,
one of carbons h, i, j, k, or m are independently substituted with =O; or,
one of carbons a, b, c, d, e, f, g, h, i, j, k or m are substituted with:

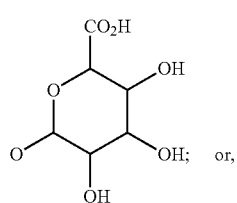

two of carbons a, b, c, d, e, f, g, h, i, j, k or in are each independently substituted with OH and:

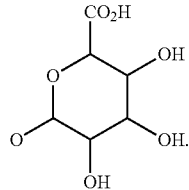 [SMILES: O=C(O)C1OC(O)C(O)C(O)C1O]

provided that the compound is not selected from:
3-(4-(7H-pyrrolo[2,3-d]pyrimidin-4-yl)-1H-pyrazol-1-yl)-3-(3-hydroxycyclopentyl)propanenitrile;
3-(4-(7H-pyrrolo[2,3-d]pyrimidin-4-yl)-1H-pyrazol-1-yl)-3-(2-hydroxycyclopentyl)propanenitrile;
3-(4-(7H-pyrrolo[2,3-d]pyrimidin-4-yl)-1H-pyrazol-1-yl)-3-(3-oxocyclopentyl)propanenitrile;
and pharmaceutically acceptable salts thereof.

In some embodiments of Formula II, 1, 2, 3, or 4 of carbons a, b, c, d, e, f, g, h, j, k or m are each independently substituted with OH. In some embodiments, one of carbons a, b, c, d, e, f, g, h, i, j, k or in are substituted with OH. In some embodiments, 2 of carbons a, b, c, d, e, f, g, h, i, j, k or m are each independently substituted with OH. In some embodiments, 3 of carbons a, b, c, d, e, f, g, h, i, j, k or m are each independently substituted with OH. In some embodiments, 4 of carbons a, b, c, d, e, f, g, h, i, j, k or in are each independently substituted with OH.

In some embodiments, one of carbons h, i, j, k, or m are substituted with =O.

In some embodiments, one of carbons a, b, c, d, e, f, g, h, i, j, k or m are substituted with:

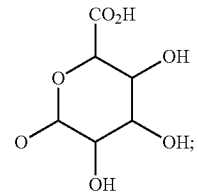 [SMILES: O=C(O)C1OC(O)C(O)C(O)C1O]

In some embodiments, one of carbons f, g, h, i, j, k or m are substituted with:

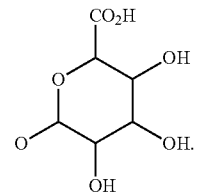 [SMILES: O=C(O)C1OC(O)C(O)C(O)C1O]

In some embodiments, two of carbons a, b, c, d, e, f, g, h, i, j, k or m are each independently substituted by OH and one of carbons a, b, c, d, e, f, g, h, i, j, k or m are substituted with:

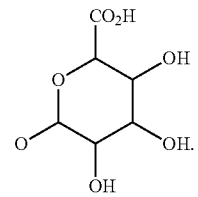 [SMILES: O=C(O)C1OC(O)C(O)C(O)C1O]

In some embodiments:
carbon m is not substituted with a OH, =O, or

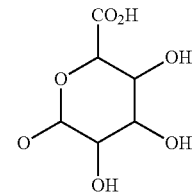 [SMILES: O=C(O)C1OC(O)C(O)C(O)C1O]

group; and
carbon f is not substituted with a OH or

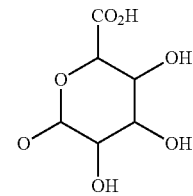 [SMILES: O=C(O)C1OC(O)C(O)C(O)C1O]

group.

In some embodiments:
carbon m is not substituted with a OH or =O group; and
carbon f is not substituted with a OH group.

Each of the aforementioned embodiments assumes that the rules for proper valency are adhered to.

In some embodiments, the compound is selected from:

6-(3-(1-(4-(7H-pyrrolo[2,3-d]pyrimidin-4-yl)-1H-pyrazol-1-yl)-2-cyanoethyl)cyclopentyloxy)-3,4,5-trihydroxytetrahydro-2H-pyran-2-carboxylic acid;

3-(4-(7H-pyrrolo[2,3-d]pyrimidin-4-yl)-1H-pyrazol-1-yl)-3-(1,2-dihydroxycyclopentyl)propanenitrile; and 3-(4-(7H-pyrrolo[2,3-d]pyrimidin-4-yl)-1H-pyrazol-1-yl)-3-(1-hydroxycyclopentyl)propanenitrile;

or a pharmaceutically acceptable salt of any of the aforementioned.

In some embodiments, the compound is selected from:

3-(4-(7H-pyrrolo[2,3-d]pyrimidin-4-yl)-1H-pyrazol-1-yl)-3-(1-hydroxycyclopentyl)propanenitrile;

3-(4-(7H-pyrrolo[2,3-d]pyrimidin-4-yl)-1H-pyrazol-1-yl)-3-cyclopentyl-3-hydroxypropanenitrile;

3-(4-(7H-pyrrolo[2,3-d]pyrimidin-4-yl)-1H-pyrazol-1-yl)-3-cyclopentyl-2-hydroxypropanenitrile;

3-cyclopentyl-3-(5-hydroxy-4-(7H-pyrrolo[2,3-d]pyrimidin-4-yl)-1H-pyrazol-1-yl)propanenitrile;

3-cyclopentyl-3-(3-hydroxy-4-(7H-pyrrolo[2,3-d]pyrimidin-4-yl)-1H-pyrazol-1-yl)propanenitrile;

3-cyclopentyl-3-(4-(5-hydroxy-7H-pyrrolo[2,3-d]pyrimidin-4-yl)-1H-pyrazol-1-yl)propanenitrile;

3-cyclopentyl-3-(4-(6-hydroxy-7H-pyrrolo[2,3-d]pyrimidin-4-yl)-1H-pyrazol-1-yl)propanenitrile;

3-cyclopentyl-3-(4-(2-hydroxy-7H-pyrrolo[2,3-d]pyrimidin-4-yl)-1H-pyrazol-1-yl)propanenitrile;

3-(4-(7H-pyrrolo[2,3-d]pyrimidin-4-yl)-1H-pyrazol-1-yl)-3-(1,2-dihydroxycyclopentyl)propanenitrile;

3-cyclopentyl-3-(4-(5,6-dihydroxy-6,7-dihydro-5H-pyrrolo[2,3-d]pyrimidin-4-yl)-1H-pyrazol-1-yl)propanenitrile; and 6-(4-(1-(2-cyano-1-cyclopentylethyl)-1H-pyrazol-4-yl)-7H-pyrrolo[2,3-d]pyrimidin-7-yl)-3,4,5-trihydroxytetrahydro-2H-pyran-2-carboxylic acid;

or a pharmaceutically acceptable salt of any of the aforementioned.

In some embodiments, the compounds described herein can include the compounds shown in the charts 1-7 below, and enantiomers, diastereomers, and racemates thereof.

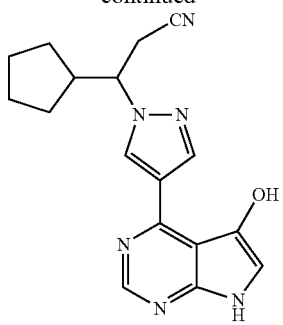

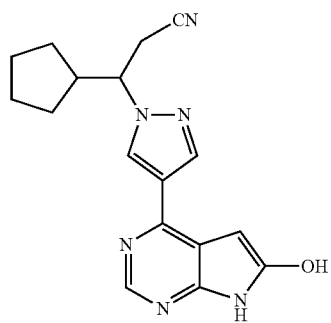

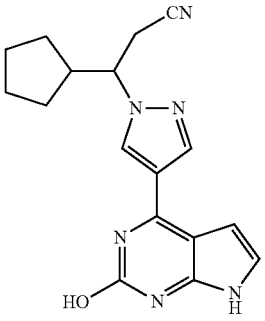

Chart 1

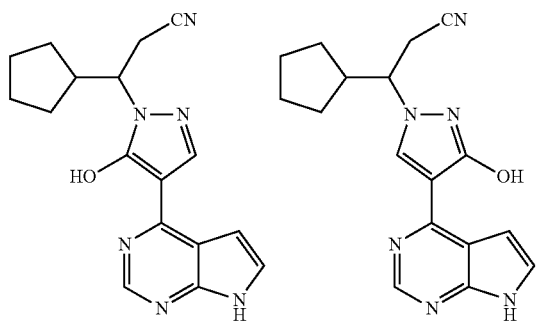

Chart 2

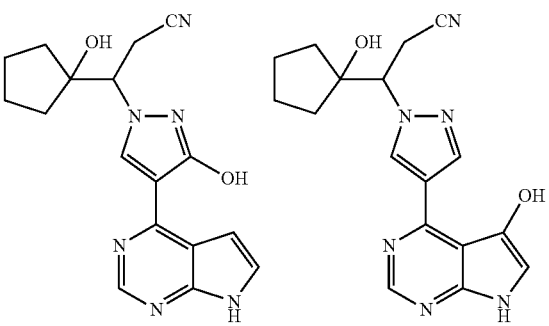

-continued
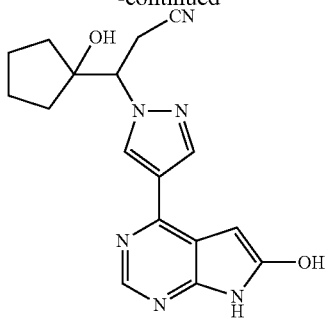
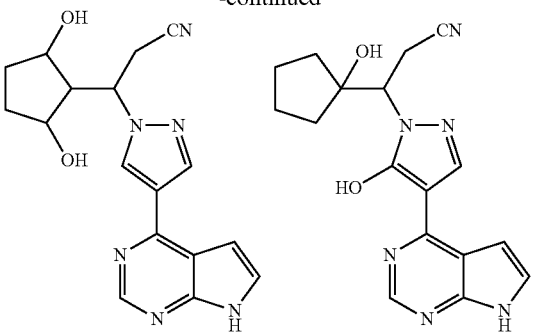
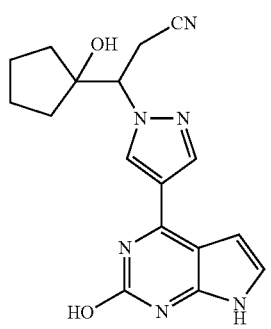
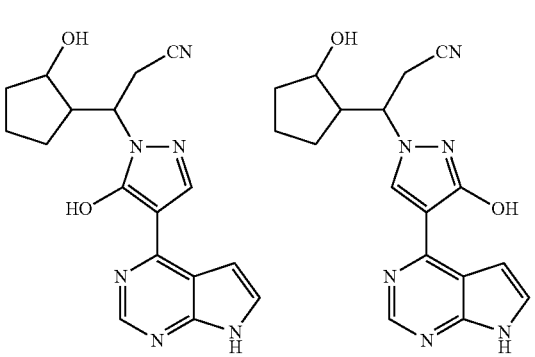
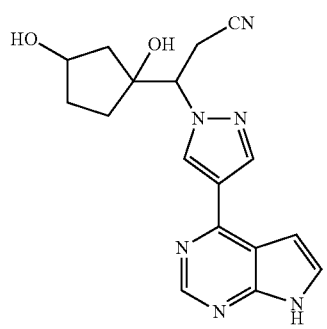
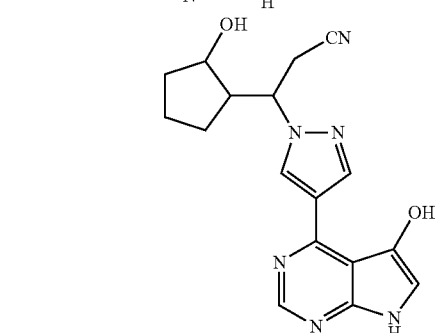
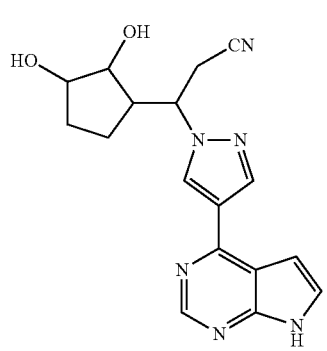
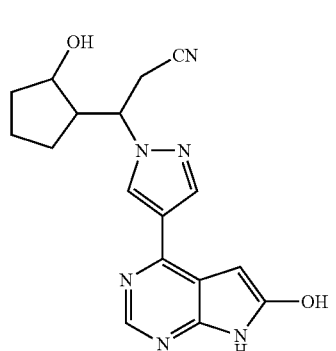
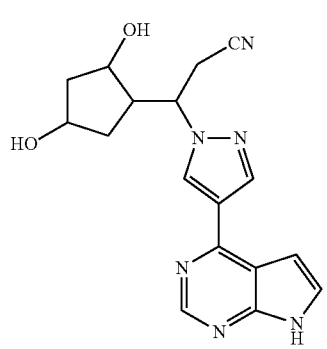
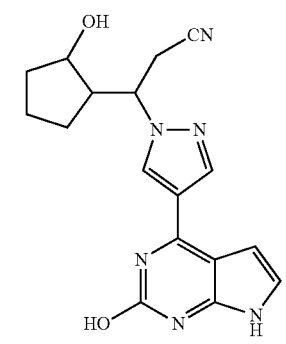

Chart 3
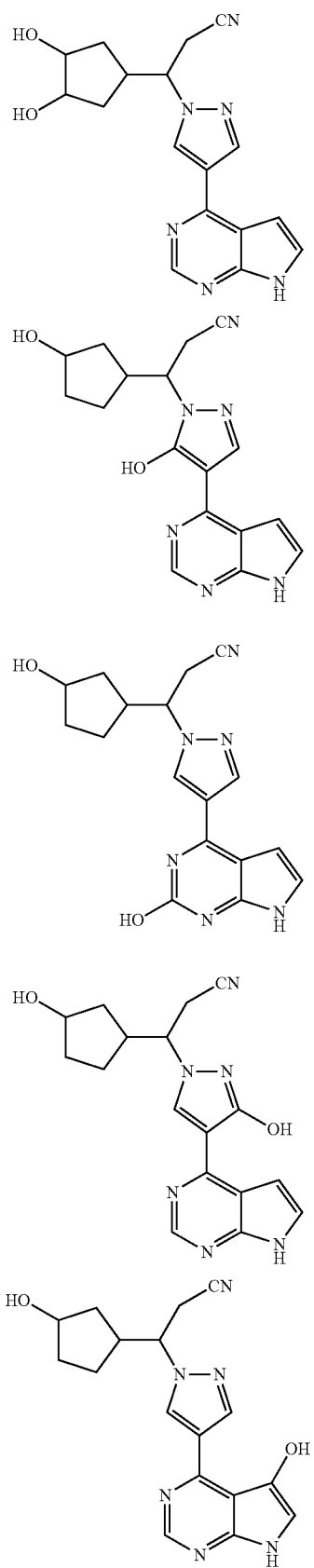
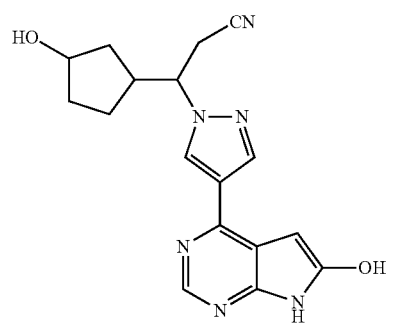 [SMILES: N#CCC(C1CCC(O)C1)n1cc(-c2ncnc3[nH]c(O)cc23)cn1]
Chart 4
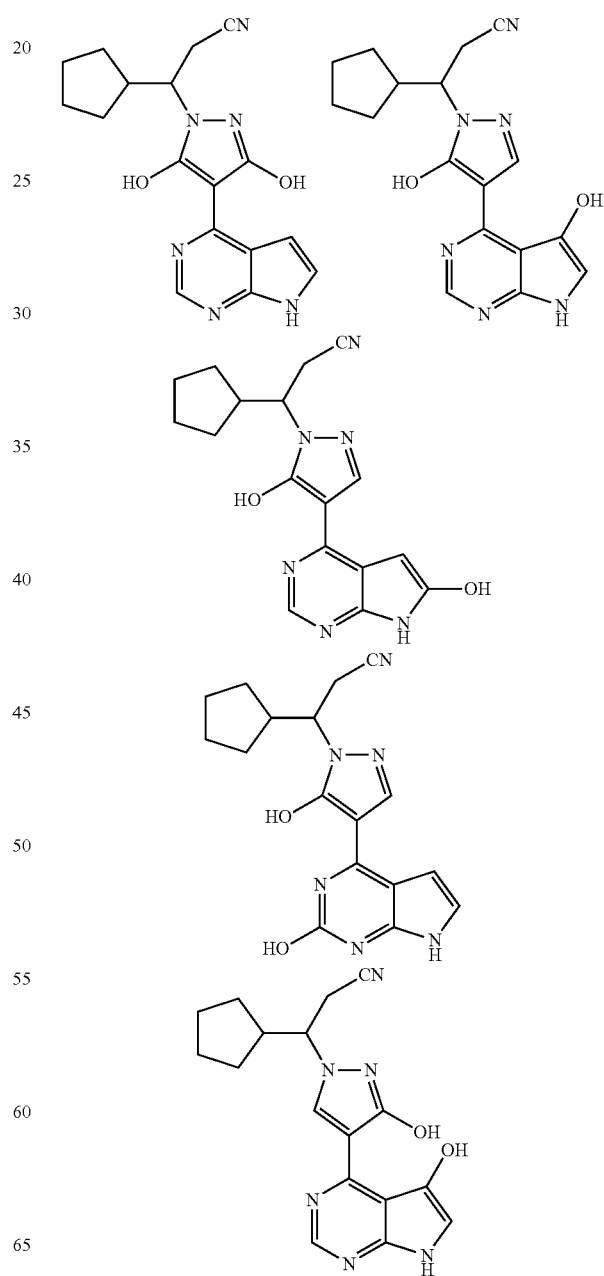

-continued
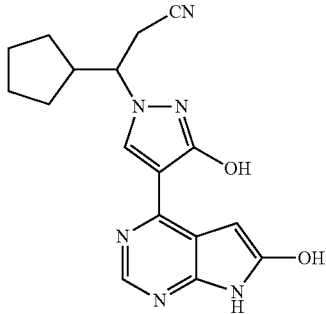
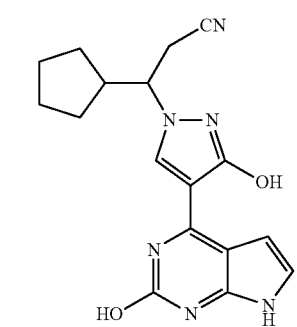
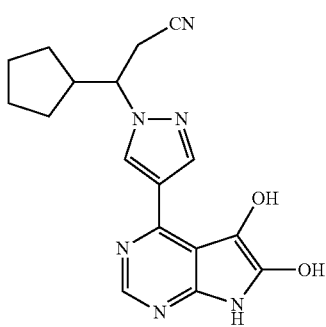
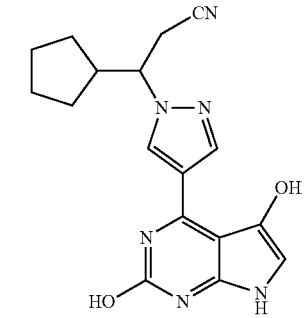
-continued
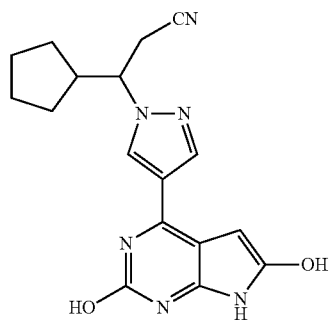
Chart 5
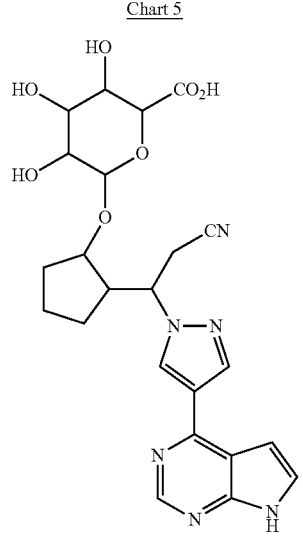
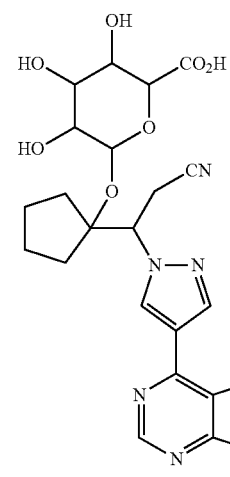

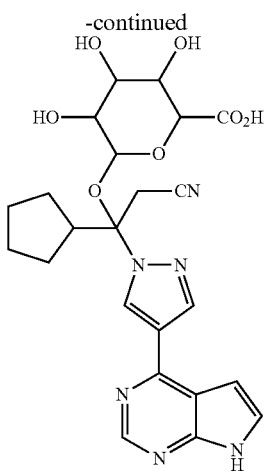
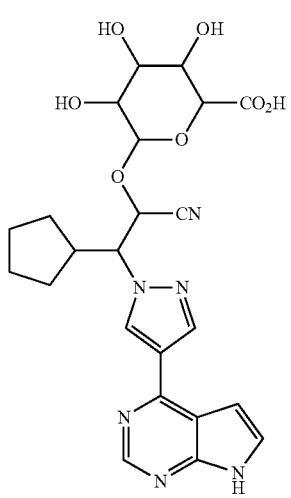 [SMILES: N#CC(OC1OC(C(=O)O)C(O)C(O)C1O)C(C1CCCC1)n1cc(-c2ncnc3[nH]ccc23)cn1]
Chart 6
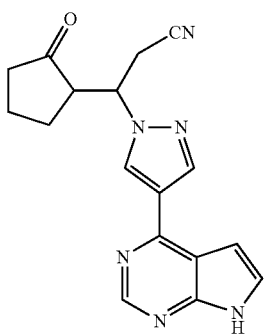
Chart 7
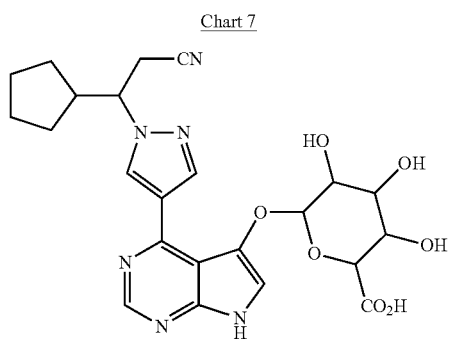
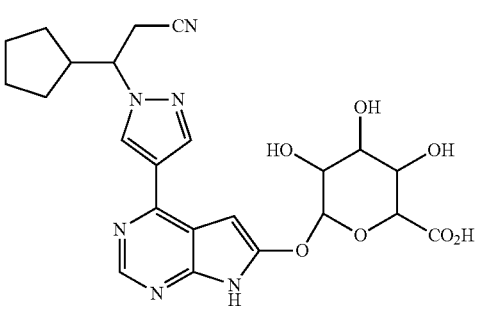
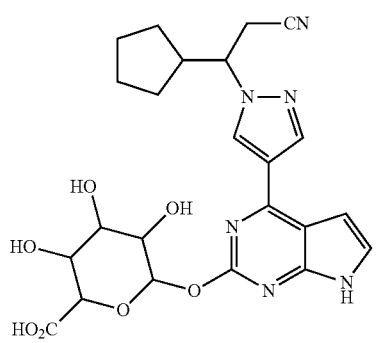
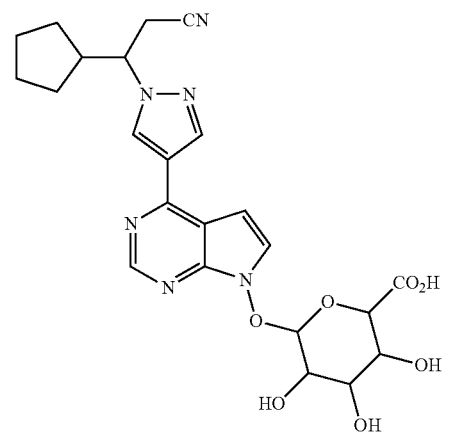
Certain metabolites are indicated in Table 1 below. Structures are intended to encompass all possible stereoisomers.

TABLE 1

| Reference* | Name | Structure |
|---|---|---|
| Metabolite 1 (3/8) | 6-(3-(1-(4-(7H-pyrrolo[2,3-d]pyrimidin-4-yl)-1H-pyrazol-1-yl)-2-cyanomethyl)cyclopentyloxy)-3,4,5-trihydroxytetrahydro-2H-pyran-2-carboxylic acid | 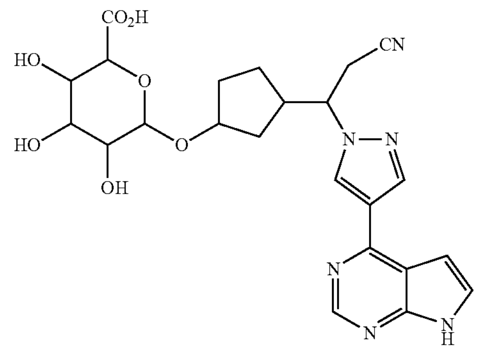 [SMILES: N#CCC(C1CCC(OC2OC(C(=O)O)C(O)C(O)C2O)C1)n1cc(-c2ncnc3[nH]ccc23)cn1] |
| Metabolite 2 (31) | 3-cyclopentyl-3-(4-(2,6-dioxo-3,5,6,7-tetrahydro-2H-pyrrolo[2,3-d]pyrimidin-4-yl)-1H-pyrazol-1-yl)propanenitrile | 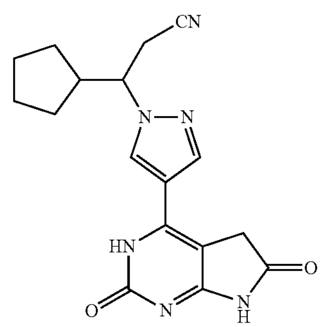 [SMILES: N#CCC(C1CCCC1)n1cc(-c2[nH]c(=O)nc3c2CC(=O)N3)cn1] |
| Metabolite 3 (32) | 3-cyclopentyl-3-(4-(2-hydroxy-5-oxo-6,7-dihydro-5H-pyrrolo[2,3-d]pyrimidin-4-yl)-1H-pyrazol-1-yl)propanenitrile | 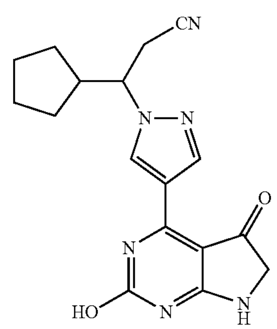 [SMILES: N#CCC(C1CCCC1)n1cc(-c2nc(O)nc3c2C(=O)CN3)cn1] |
| Metabolite 4 (35) | 3-(4-(7H-pyrrolo[2,3-d]pyrimidin-4-yl)-1H-pyrazol-1-yl)-3-(1,2-dihydroxycyclopentyl)propanenitrile | 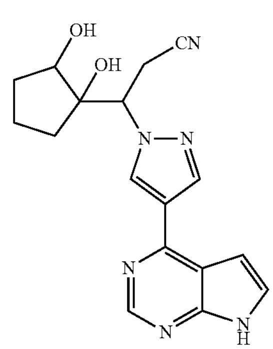 [SMILES: N#CCC(n1cc(-c2ncnc3[nH]ccc23)cn1)C1(O)CCCC1O] |

TABLE 1-continued

| Reference* | Name | Structure |
|---|---|---|
| Metabolite 5 (36) | 3-(4-(7H-pyrrolo[2,3-d]pyrimidin-4-yl)-1H-pyrazol-1-yl)-3-(1-hydroxycyclopentyl)propanenitrile | 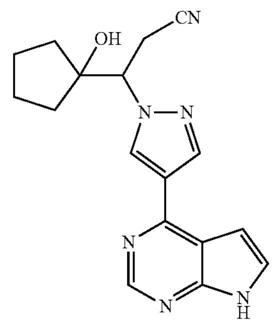 [SMILES: N#CCC(n1cc(-c2ncnc3[nH]ccc23)cn1)C1(O)CCCC1] |
| Metabolite 6 (37) | 3-cyclopentyl-3-(4-(6-oxo-6,7-dihydro-5H-pyrrolo[2,3-d]pyrimidin-4-yl)-1H-pyrazol-1-yl)propanenitrile | 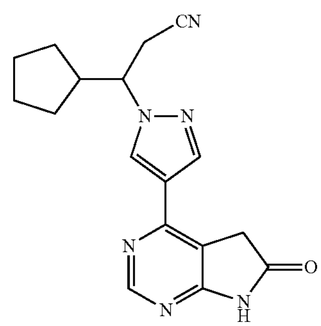 [SMILES: N#CCC(C1CCCC1)n1cc(-c2ncnc3c2CC(=O)N3)cn1] |
| Metabolite 7 (38) | 3-(3-hydroxycyclopentyl)-3-(4-(6-oxo-6,7-dihydro-5H-pyrrolo[2,3-d]pyrimidin-4-yl)-1H-pyrazol-1-yl)propanenitrile | 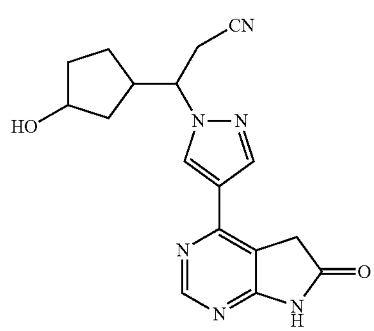 [SMILES: N#CCC(C1CCC(O)C1)n1cc(-c2ncnc3c2CC(=O)N3)cn1] |
| Metabolite 8 | 3-(4-(7H-pyrrolo[2,3-d]pyrimidin-4-yl)-1H-pyrazol-1-yl)-3-(3-hydroxycyclopentyl)propanenitrile | 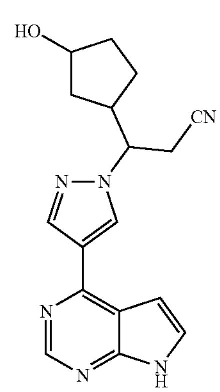 [SMILES: N#CCC(C1CCC(O)C1)n1cc(-c2ncnc3[nH]ccc23)cn1] |

TABLE 1-continued

| Reference* | Name | Structure |
|---|---|---|
| Metabolite 9 | 3-(4-(7H-pyrrolo[2,3-d]pyrimidin-4-yl)-1H-pyrazol-1-yl)-3-(2-hydroxycyclopentyl)propanenitrile | 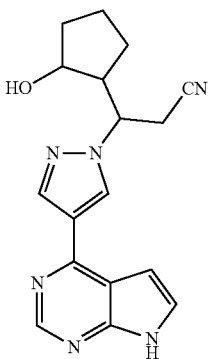 [SMILES: N#CCC(C1CCCC1O)n1cc(-c2ncnc3[nH]ccc23)cn1] |

*The numbers in parentheses refer to the compound numbers in Table 2 (infra)

Compounds described herein are metabolites of (R)-3-(4-(7H-pyrrolo[2,3-d]pyrimidin-4-yl)-1H-pyrazol-1-yl)-3-cyclopentylpropanenitrile. The metabolites of the invention were isolated from human, rat or dog urine samples collected from pharmacokinetic and toxicokinetic studies of the JAK inhibitor (R)-3-(4-(7H-pyrrolo[2,3-d]pyrimidin-4-yl)-1H-pyrazol-1-yl)-3-cyclopentylpropanenitrile (Compound I). Certain metabolites may be JAK inhibitors, and can have advantageous properties related to significantly higher free fractions and higher metabolic stability in human microsomes compared with Compound I. The present metabolites may desirably have a longer elimination half-life in humans than does Compound I.

In some embodiments, the metabolites of the invention are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the metabolite.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds described herein are asymmetric (e.g., having one or more stereocenters). All stereoisomers, such as enantiomers and diastereomers, are intended unless otherwise indicated. Methods on how to prepare optically active forms from optically active starting materials are known in the art, such as by resolution of racemic mixtures or by stereoselective synthesis.

Compounds described herein also include all isotopes of atoms occurring in the metabolites. Isotopes include those atoms having the same atomic number but different mass numbers. For example, isotopes of hydrogen include tritium and deuterium. The compounds may also include solvates and hydrates of the compounds or salt forms.

The term, "compound," as used herein is meant to include all stereoisomers, geometric iosomers, tautomers, and isotopes of the structures depicted.

Synthesis

Compounds described herein, including salts thereof, can be prepared using known organic synthesis techniques and can be synthesized according to any of numerous possible synthetic routes.

The reactions for preparing compounds described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

Compounds described herein can be prepared according to numerous preparatory routes known in the literature. For example, compounds described herein may be made by processes analogous to those described in U.S. Ser. No. 11/637,545 (US 2007/0135461), filed Dec. 12, 2006; U.S. Ser. No. 12/138,082 (US 2009/0181959), filed Jul. 16, 2009; and U.S. Ser. No. 12/137,883 (US 2008/0312258), filed Jun. 12, 2008, each of which is incorporated herein by reference in its entirety. Example synthetic methods for preparing compounds described herein are provided in the Schemes below.

As shown in Scheme 1, synthesis of compound 32 starts with 4-chloro pyrrolopyrimidine S1. The Suzuki coupling of S1 with the pyrazole boronate S2 under basic conditions in the presence of Pd(0) catalyst may provide the tricyclic compound S3 which is subsequently converted selectively to the iodo compound S4 using N-iodosuccinimide. The iodo compound S4 is transformed to the corresponding acetate S5. Treatment of S5 with 4M hydrogen bromide in acetic acid provides S6 with the desired oxidation in the pyrrole ring along with the deprotection of the methoxy group to the free hydroxyl. The cyano group which was hydrolyzed to the amide under these conditions is reinstalled in 32 by treatment of S6 with trichloroacetyl chloride and triethylamine to effect the dehydration.

Scheme 1

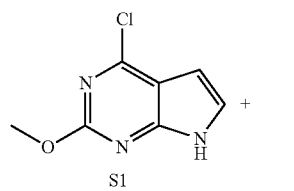

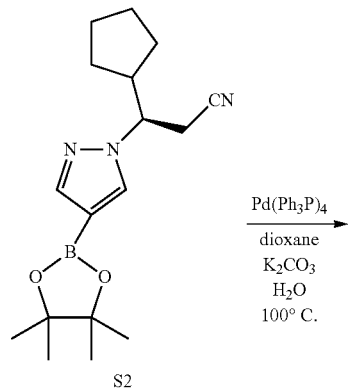

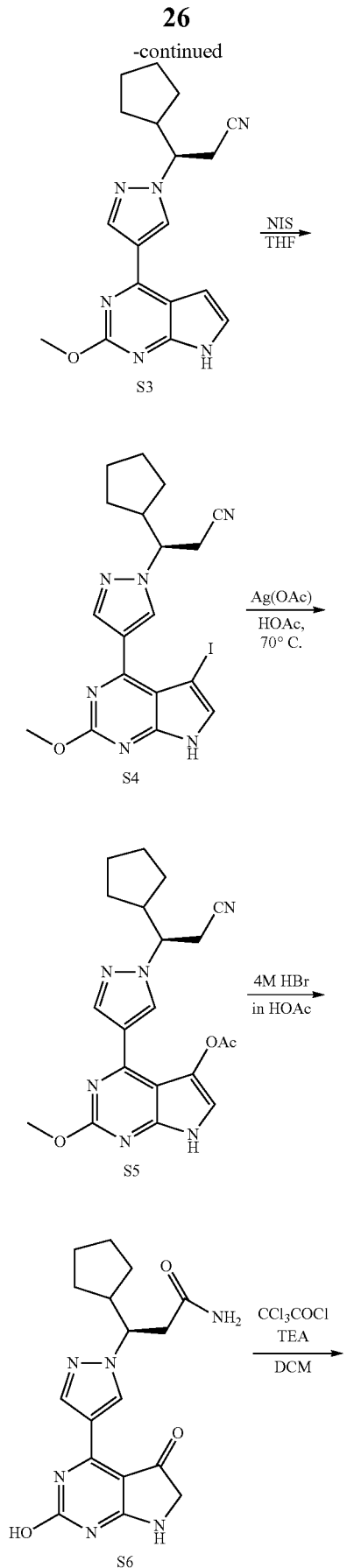

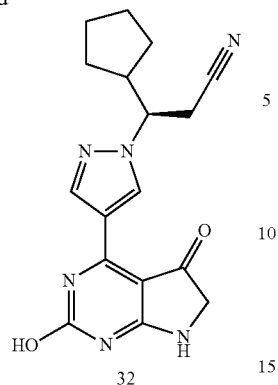

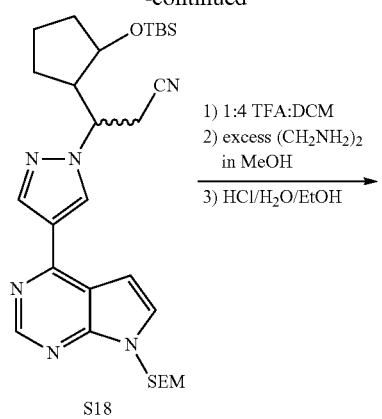

The mono-hydroxylated compound 42 (metabolite 8) has been reported in U.S. Ser. No. 12/137,883, filed Jun. 12, 2008. Further, compounds having a hydroxyl group on the cyclopentyl ring may also be synthesized as in Scheme 2. For example, the commercially available racemic S14 in which the alcohol is protected followed by reduction of the carboxylic ester to the aldehyde followed by an olefination of the aldehyde to provide S17. Conjugate addition of S9 to S17 under basic conditions provides S18 from which the protecting groups on the alcohol and pyrrole ring are removed sequentially to provide a mixture of diastereomers which are then separated using multiple chiral HPLC columns to provide the four diastereomers of S19. In some embodiments, the present invention provides a process of making compound 42, or a pharmaceutically acceptable salt thereof, comprising one or more of the steps in Scheme 2.

Scheme 2

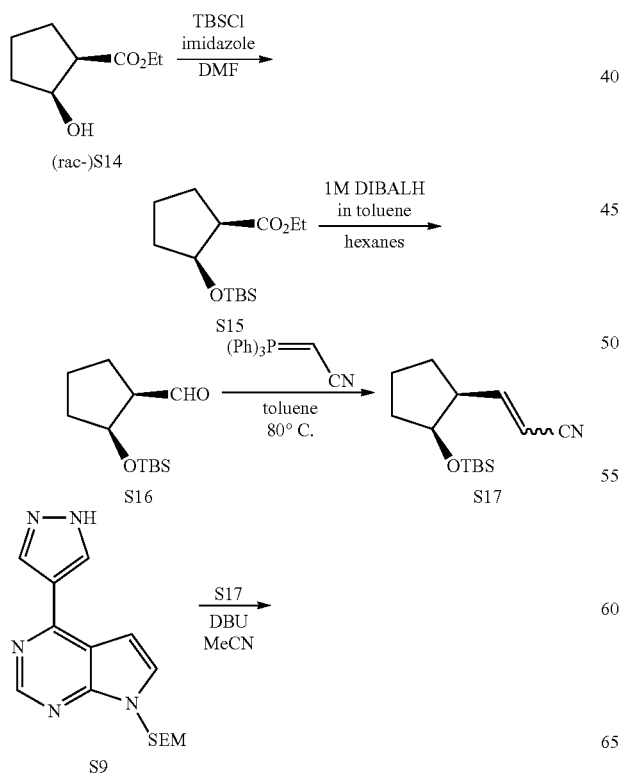

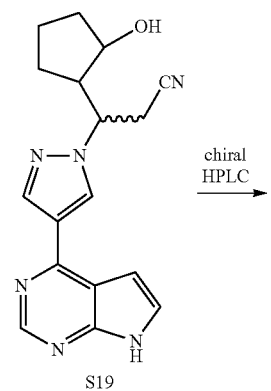

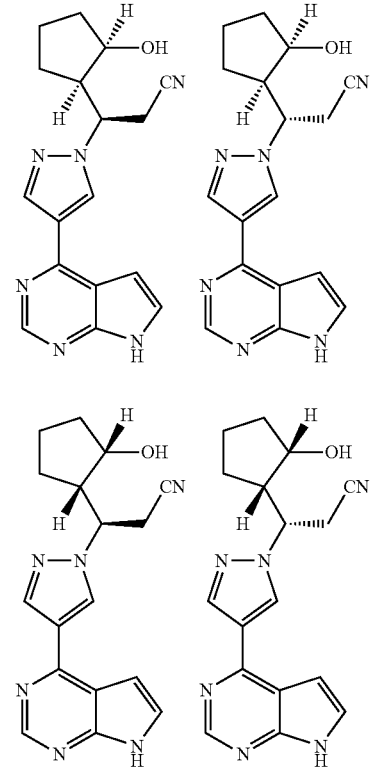

Another example of the mono-hydroxylated compound 36 is obtained by the sequence shown in Scheme 3. The protected cycanohydrin S31 can be reduced with DIBAL to the corresponding aldehyde followed by the olefination with the phosphonate such as S7 to provide the crotontirile S33. Conjugate addition of S9 to S33 under basic conditions provides S34 from which the protecting group on the pyrrole ring is removed to provide a mixture of diastereomers which can then be separated using multiple chiral HPLC columns to provide the individual stereoisomers of 36.

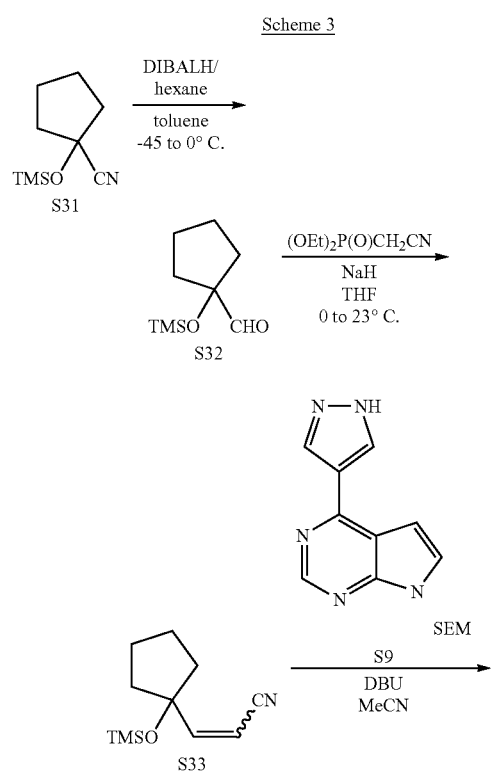

Scheme 3

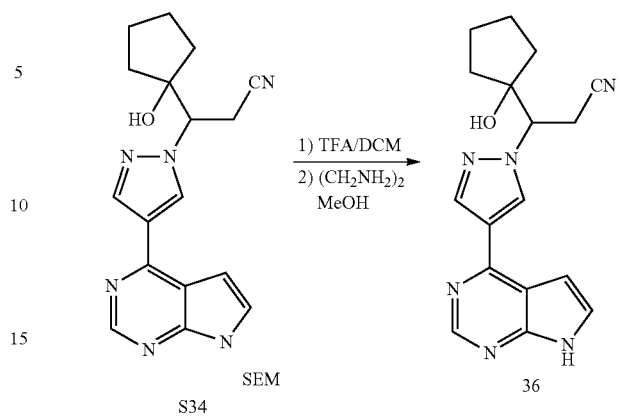

The dihydroxylated metabolites may be obtained in a similar fashion as shown in Scheme 4: cyclopentene carboxaldehyde S6A may be treated directly with the ylid S7 to give the crotonitrile derivative S8. The nitrile S8 then can be reacted with the pyrazole S9 in the presence of a base such as DBU to give S10 as a mixture of diastereomers, which can be dihydroxylated with osmium tetroxide to provide the cis-alcohols cis-S12A, after removal of the SEM group. The individual stereoisomers of this mixture (cis-S12A) may be separated by chiral chromatography to give the enantiomerically pure alcohols. The trans-S12A may be obtained by first epoxidizing the olefin with m-CPBA followed by opening up the epoxide under acidic conditions. The individual stereoisomers of this mixture (trans-S12A) may be separated by chiral chromatography to give the enantiomerically pure alcohols. The same synthetic route may be adapted to obtain the isomeric S12B and S12C by replacing the starting aldehyde S6A with S6B and S6C.

Scheme 4

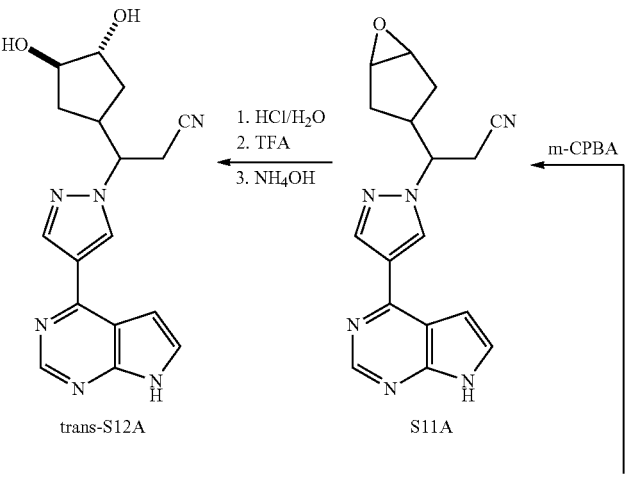

-continued

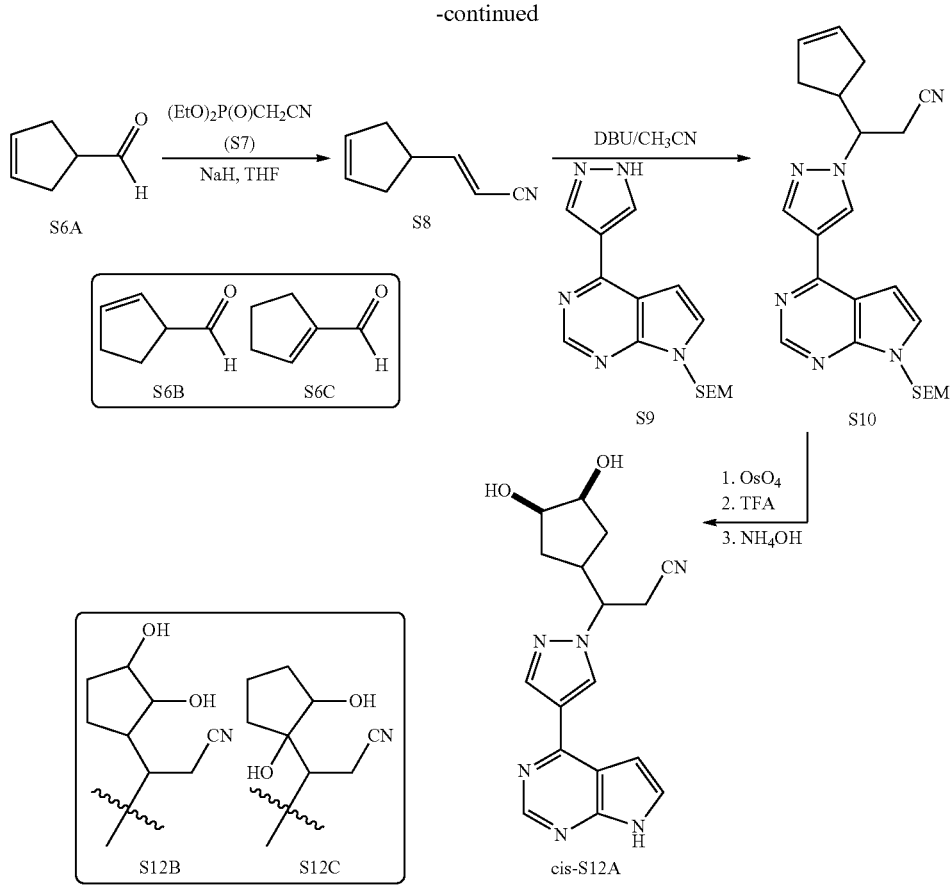

A combination of the methods described above along with those described in U.S. patent application Ser. No. 11/637,545, filed Dec. 12, 2006; and in U.S. patent application Ser. No. 12/137,883, filed Jun. 12, 2008, which are incorporated herein in its entirety, may be utilized to obtain the trihydroxy compounds of the invention. For example, the hydroxy and dihydroxy compounds described herein may be oxidized under Swern oxidation conditions described in U.S. patent application Ser. No. 12/137,883, filed Jun. 12, 2008. The glucuronides of metabolites containing hydroxyl groups may be synthesized according to the procedure of Suzuki et al. (Bioorg. Med. Chem. Lett. (1999), 9(5), 659-662 which is incorporated herein in its entirety).

Methods

Certain compounds described herein may modulate activity of one or more Janus kinases (JAKs). The term "modulate" is meant to refer to an ability to increase or decrease the activity of one or more members of the JAK family of kinases. Accordingly, certain compounds described herein can be used in methods of modulating a JAK by contacting the JAK with any one or more of the compounds or compositions described herein. In some embodiments, certain compounds may act as inhibitors of one or more JAKs. In some embodiments, certain compounds described herein can act to stimulate the activity of one or more JAKs. In further embodiments, certain compounds may be used to modulate activity of a JAK in an individual in need of modulation of the receptor by administering a modulating amount of a compound of the invention.

JAKs to which compounds bind and/or modulate may include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3.

In some embodiments, active compounds may be selective. By "selective" is meant that the compound binds to or inhibits a JAK with greater affinity or potency, respectively, compared to at least one other JAK (e.g., selective inhibitors of JAK1 or JAK2 over JAK3 and/or TYK2). In some embodiments, selective means selective inhibition of JAK2 (e.g., over JAK1, JAK3 and TYK2). Without wishing to be bound by theory, because inhibitors of JAK3 can lead to immunosuppressive effects, a compound which is selective for JAK2 over JAK3 and which is useful in the treatment of cancer (such as multiple myeloma, for example) can offer the additional advantage of having fewer immunosuppressive side effects. Selectivity may be at least about 5-fold, at least about 10-fold, at least about 20-fold, at least about 50-fold, at least about 100-fold, at least about 200-fold, at least about 500-fold or at least about 1000-fold. Selectivity may be measured by methods routine in the art. In some embodiments, selectivity may be tested at the Km of each enzyme. In some embodiments, selectivity for JAK2 over JAK3 can be determined by the cellular ATP concentration.

Another aspect of the present invention pertains to methods of treating a JAK-associated disease or disorder in an individual (e.g., patient) by administering to the individual in need of such treatment a therapeutically effective amount or dose of a certain compound described herein or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, skin rash, skin irritation, skin sensitization (e.g., contact dermatitis, allergic contact dermatitis, or allergic contact sensitization). For example, certain substances including some pharmaceuticals when topically applied can cause skin sensitization. In some embodiments, co-administration or sequential administration of at least one JAK inhibitor together with the agent causing unwanted sensitization can be helpful in treating such unwanted sensitization or dermatitis. In some embodiments, the skin disorder is treated by topical administration of at least one JAK inhibitor.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, acute myelogenous leukemia (AML) or multiple myeloma), and skin cancer such as cutaneous T-cell lymphoma (CTCL) and cutaneous B-cell lymphoma. Example cutaneous T-cell lymphomas include Sezary syndrome and mycosis fungoides.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), systemic mast cell disease (SMCD), and the like.

Further JAK-associated diseases include inflammation and inflammatory diseases. Example inflammatory diseases include sarcoidosis, inflammatory diseases of the eye (e.g., dry eye, iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. Other inflammatory diseases treatable by JAK inhibitors include systemic inflammatory response syndrome (SIRS) and septic shock.

As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface,* 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

JAK inhibitors can further be used to treat ischemia reperfusion injuries or a disease or condition related to an inflammatory ischemic event such as stroke or cardiac arrest. JAK inhibitors can further be used to treat anorexia, cachexia, or fatigue such as that resulting from or associated with cancer. JAK inhibitors can further be used to treat restenosis, sclerodermitis, or fibrosis. JAK inhibitors can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2.

JAK inhibitors can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

As used herein, the term "contacting" refers to the bringing together of indicated moieties in an in vitro system or an in vivo system. For example, "contacting" a JAK with a compound includes the administration of a compound of the present invention to an individual or patient, such as a human, having a JAK, as well as, for example, introducing a compound into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The levels of metabolites in a patient after administration of compound I in an individual can be measured and profiled. Such metabolite profile can then be used to adjust the dosage regimens (e.g., for administration of compound I) in that individual. For example, faster clearance of compound I as shown by levels of various metabolites after a given time period may mean that initial dosages should be adjusted upwards.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, or other agents can be used in combination with certain compounds described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, one or more compounds described herein may be used in combination with one or more other kinase inhibitors including imatinib, particularly for treating patients resistant to imatinib or other kinase inhibitors.

In some embodiments, one or more compounds can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a compound of the present invention with an additional agent. Furthermore, resistance of multiple myeloma cells to agents such as dexamethasone may be reversible upon treatment with a compound of the present invention. The agents can be combined with the JAK inhibitor in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more compounds with other therapeutic agents can be administered to a patient prior to, during, and/or after a bone marrow transplant or stein cell transplant.

Pharmaceutical Formulations and Dosage Forms

When employed as pharmaceuticals, the compounds described herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. In some embodiments, the composition is suitable for oral administration. Parenteral administration includes intravenous, intraarterial, subcutaneous, intraperitoneal, intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds described herein in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The active ingredient may be milled using known milling procedures such as wet milling to obtain a particle size appropriate for tablet formation and for other formulation types. Finely divided (nanoparticulate) preparations of the active ingredient can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound in a pharmaceutical composition can vary depending upon a number of factors including dosage, chemical characteristics (e.g., hydrophobicity), and the route of administration. For example, the compounds can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is an topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly(dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", Asian J. Pharm., pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly (dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al. (ibid), In some embodiments, the film is a soft-contact lens, such as ones made from copolymers of N,N-diethylacrylamide and methacrylic acid crosslinked with ethyleneglycol dimethacrylate.

In some embodiments, the ophthalmic composition comprises microspheres or nanoparticles. In some embodiment, the microspheres comprise gelatin. In some embodiments, the microspheres are injected to the posterior segment of the eye, in the chroroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled version of certain compounds described herein (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds. An "isotopically" or "radio-labeled" compound is a compound described herein where one or more atoms are replaced or substituted by an atom having an atomic mass or mass number different from the atomic mass or mass number typically found in nature (i.e., naturally occurring). Suitable radionuclides that may be incorporated in compounds described herein include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro metalloprotease labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

The present invention can further include synthetic methods for incorporating radio-isotopes into compounds described herein. Synthetic methods for incorporating radio-isotopes into organic compounds are well known in the art, and a person of ordinary skill in the art will readily recognize the methods applicable for the compounds described herein.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of an active compound. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

(R)-3-cyclopentyl-3-[4-(2-hydroxy-5-oxo-6,7-dihydro-5,1-pyrrolo[2,3-d]pyrimidin-4-yl)-1H-pyrazol-1-yl]propanenitrile

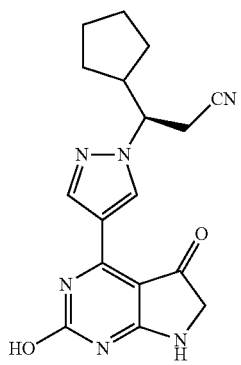 [SMILES: N#CC[C@H](C1CCCC1)n1cc(-c2nc(O)nc3c2C(=O)CN3)cn1]

Step 1. (R)-3-cyclopentyl-3-[4-(2-methoxy-7H-pyrrolo[2,3-d]pyrimidin-4-yl)-1H-pyrazol-1-yl]propanenitrile

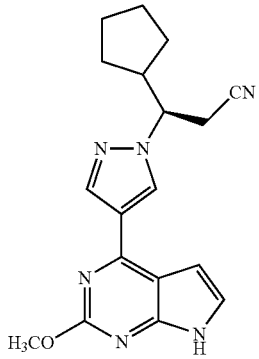 [SMILES: COc1nc(-c2cnn([C@H](CC#N)C3CCCC3)c2)c2cc[nH]c2n1]

4-Chloro-2-methoxy-7H-pyrrolo[2,3-d]pyrimidine (0.4 g, 2.18 mmol, Toronto Research Chemicals) and (R)-3-cyclopentyl-3-[4-(4,4,5,5-tetramethyl-1,3,2-dioxaborolan-2-yl)-1H-pyrazol-1-yl]propanenitrile (0.824 g, 2.61 mmol, prepared as described in Org. Lett., 2009, 11(9), 1999-2002.) were dissolved in 1,4-dioxane (4 mL) and potassium carbonate (0.903 g, 6.54 mmol) in water (2 mL) was added. The mixture was degassed and tetrakis(triphenylphosphine)palladium(0) (0.126 g, 0.109 mmol) was added. The reaction mixture was heated to 100° C. for 16 h. The reaction mixture was partitioned between water and ethyl acetate. The aqueous layer was extracted with ethyl acetate three times. The combined extracts were dried over sodium sulfate, decanted and concentrated. Flash column chromatography, eluting with a gradient from 0-10% MeOH in methylene chloride was used to purify the product (670 mg, 91%). $^1$H NMR (300 MHz, CD$_3$OD): δ 8.59 (s, 1H), 8.35 (s, 1H), 7.24 (d, 1H), 6.81 (d, 1H), 4.47 (dt, 1H), 4.04 (s, 3H), 3.21 (dd, 1H), 3.10 (dd, 1H), 2.62-2.44 (m, 1H), 2.02-1.86 (m, 1H), 1.81-1.20 (m, 7H); LCMS (M+H)$^+$: 337.0.

Step 2. (R)-3-cyclopentyl-3-[4-(5-iodo-2-methoxy-7H-pyrrolo[2,3-d]pyrimidin-4-yl)-1H-pyrazol-1-yl]propanenitrile

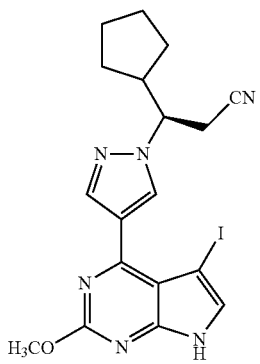 [SMILES: COc1nc(-c2cnn([C@H](CC#N)C3CCCC3)c2)c2c(I)c[nH]c2n1]

To a solution of 3-cyclopentyl-3-[4-(2-methoxy-7H-pyrrolo[2,3-d]pyrimidin-4-yl)-1H-pyrazol-1-yl]propanenitrile (0.532 g, 1.58 mmol) in tetrahydrofuran (20 mL) was added N-iodosuccinimide (0.36 g, 1.6 mmol). The reaction was stirred for 30 min and the solvent was removed in vacuo. The residue was purified by flash column chromatography, eluting with a gradient from 0-65% ethyl acetate in hexanes to afford a yellow solid (250 mg, 34%). $^1$H NMR (300 MHz, CDCl$_3$): δ 10.31 (br s, 1H), 8.27 (s, 1H), 8.23 (s, 1H), 7.29 (s, 1H), 4.34-4.21 (m, 1H), 4.06 (s, 3H), 3.14 (dd, 1H), 3.03-2.90 (m, 1H), 2.66-2.49 (m, 1H), 2.02-1.17 (m, 8H); LCMS (M+H)$^+$: 463.0.

Step 3. (R)-4-[1-(2-cyano-1-cyclopentylethyl)-1H-pyrazol-4-yl]-2-methoxy-7H-pyrrolo[2,3-d]pyrimidin-5-yl acetate

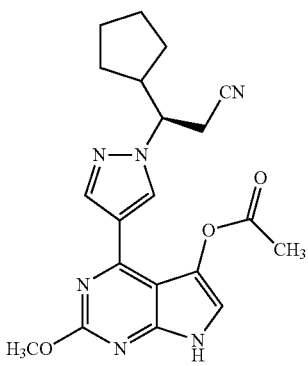 [SMILES: COc1nc(-c2cnn([C@H](CC#N)C3CCCC3)c2)c2c(OC(C)=O)c[nH]c2n1]

A solution of 3-cyclopentyl-3-[4-(5-iodo-2-methoxy-7H-pyrrolo[2,3-d]pyrimidin-4-yl)-1H-pyrazol-1-yl]propanenitrile (0.25 g, 0.54 mmol) in acetic acid (3 mL) was treated with silver acetate (0.27 g, 1.6 mmol) and heated to 70° C. for 16 h. The mixture was filtered, rinsed with MeCN, water was added to the filtrate and this mixture was stirred for 20 min, Solid sodium chloride was added to this solution. The product was obtained by extraction of this aqueous mixture with three portions of ethyl acetate. The combined extracts were dried over sodium sulfate, decanted and concentrated. A portion of the product was used in the hydrolysis step (Step 4) without further purification. $^1$H NMR (300 MHz, CDCl$_3$): δ 9.87 (br s, 1H), 8.39 (s, 1H), 8.37 (s, 1H), 7.33 (s, 1H), 4.22 (dt, 1H), 4.06 (s, 3H), 3.14 (dd, 1H), 2.94 (dd, 1H), 2.64-2.47 (m, 1H), 2.36 (s, 3H), 2.03-1.86 (m, 1H), 1.79-1.12 (m, 7H); LCMS (M+H)$^+$: 395.1.

Step 4. (R)-3-cyclopentyl-3-[4-(2-hydroxy-5-oxo-6,7-dihydro-5H-pyrrolo[2,3-d]pyrimidin-4-yl)-1H-pyrazol-1-yl]propanamide

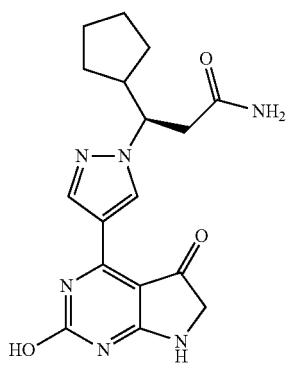 [SMILES: NC(=O)C[C@H](C1CCCC1)n1cc(-c2nc(O)nc3c2C(=O)CN3)cn1]

4 M of HBr in acetic acid (2 mL, 8 mmol) was added to 4-[1-(2-cyano-1-cyclopentylethyl)-1H-pyrazol-4-yl]-2-methoxy-7H-pyrrolo[2,3-d]pyrimidin-5-yl acetate (0.050 g, 0.13 mmol) and the reaction was stirred for 1 h. Volatiles were removed in vacuo. The residue was reconstituted and preparative HPLC-MS (eluting with a gradient of MeCN/H$_2$O containing 0.15% NH$_4$OH) was used to afford purified product (12 mg, 26%). $^1$H NMR (500 MHz, d$_6$-DMSO): δ 9.20 (s, 1H), 8.69 (s, 1H), 7.34 (s, 1H), 6.75 (s, 1H), 4.49 (dt, 1H), 3.89 (s, 2H), 2.80 (dd, 1H), 2.64 (dd, 1H), 2.36-2.26 (m, 1H), 1.83-1.74 (m, 1H), 1.63-1.36 (m, 4H), 1.32-1.20 (m, 2H), 1.15-1.05 (m, 1H); LCMS (M+H)$^+$: 357.0.

Step 5. (R)-3-cyclopentyl-3-[4-(2-hydroxy-5-oxo-6,7-dihydro-5H-pyrrolo[2,3-d]pyrimidin-4-yl)-1H-pyrazol-1-yl]propanenitrile To a solution of 3-cyclopentyl-3-[4-(2-hydroxy-5-oxo-6,7-dihydro-5H-pyrrolo[2,3-d]pyrimidin-4-yl)-1H-pyrazol-1-yl]propanamide (0.006 g, 0.02 mmol) in methylene chloride (0.5 mL) containing triethylamine (20 TL, 0.2 mmol) was added trichloroacetyl chloride (20 TL, 0.2 mmol). When the reaction was complete, preparative HPLC-MS (MeCN/H$_2$O containing 0.15% NH$_4$OH) was used to afford purified product (3 mg, 52%). $^1$H NMR (400 MHz, d$_6$-DMSO): δ 11.39 (br s, 1H), 9.37 (s, 1H), 8.77 (s, 1H), 8.63 (s, 1H), 4.68-4.59 (m, 1H), 3.94 (s, 2H), 3.19-3.15 (m, 2H), 2.42-2.30 (m, 1H), 1.86-1.75 (m, 1H), 1.69-1.20 (m, 6H), 1.18-1.05 (m, 1H); LCMS (M+H)$^+$: 339.1.

Example 2

(3R)- and (3S)-3-[(1R,2R)-2-hydroxycyclopentyl]-3-[4-(7H-pyrrolo[2,3-d]pyrimidin-4-yl)-1H-pyrazol-1-yl]propanenitrile and (3R)- and (3S)-3-[(1S,2S)-2-hydroxycyclopentyl]-3-[4-(7H-pyrrolo[2,3-d]pyrimidin-4-yl)-1H-pyrazol-1-yl]propanenitrile

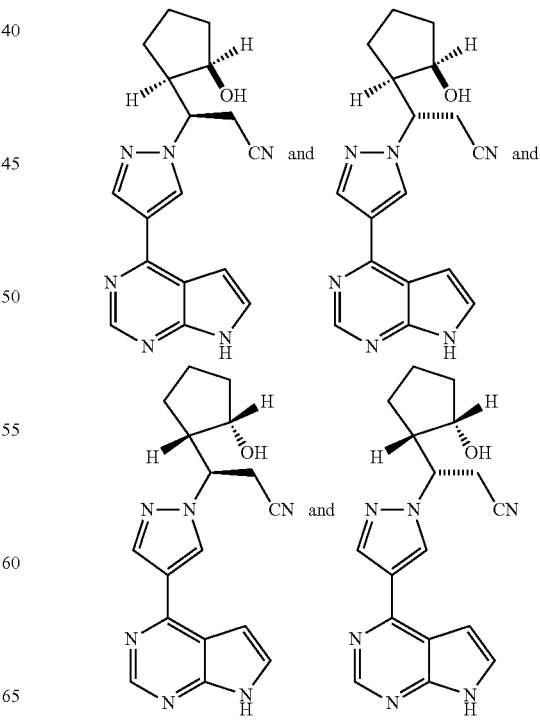

Step 1. (1S,2R)-ethyl 2-(tert-butyldimethylsiloxy) cyclopentanecarboxylate and (1R,2S)-ethyl 2-(tert-butyldimethylsilyloxy)cyclopentanecarboxylate

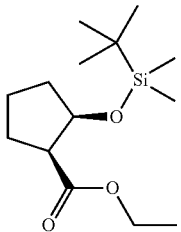 and 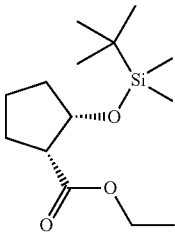

To a solution of tert-butyldimethylsilyl chloride (0.524 g, 3.48 mmol) and 1H-Imidazole (0.473 g, 6.95 mmol) in N,N-dimethylformamide (15 mL) was added ethyl cis-2-hydroxy-1-cyclopentanecarboxylate (racemic, Acros) (0.50 g, 0.0032 mol). The reaction was stirred for 16 h. Further imidazole (0.40 g, 5.8 mmol) and tert-butyldimethylsilyl chloride (0.50 g, 3.3 mmol) were added portion wise and the reaction stirred for a further 24 h. The product was extracted with hexane. The extracts were washed with water, dried over sodium sulfate, filtered and evaporated to afford racemic TBS-protected hydroxyester (0.9 g) which were used without further purification. $^1$H NMR (400 MHz, CDCl$_3$): δ 4.46 (ddd, 1H), 4.19 (dq, 1H), 4.01 (dq, 1H), 2.72 (dt, 1H), 2.22-2.11 (m, 1H), 1.96-1.49 (m, 5H), 1.26 (t, 3H), 0.84 (s, 9H), 0.03 (s, 3H), 0.01 (s, 3H).

Step 2. (1S,2R)-2-(tert-butyldimethylsilyloxy)cyclopentanecarbaldehyde and (1R,2S)-2-(tert-butyldimethylsilyloxy)cyclopentanecarbaldehyde

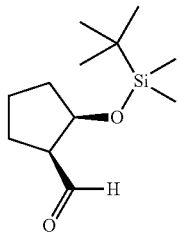 and 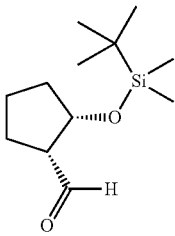

To a solution of (1S,2R)-ethyl 2-(tert-butyldimethylsilyloxy)cyclopentanecarboxylate and (1R,2S)-ethyl 2-(tert-butyldimethylsilyloxy)cyclopentanecarboxylate from Step 1 (0.86 g, 3.2 mmol) in hexanes (40 mL) at −78° C. was added drop wise a solution of 1.0 M of diisobutylaluminum hydride in toluene (3.5 mL, 3.5 mmol). The reaction mixture was stirred for 1 h at −78° C. and was quenched this temperature by the drop wise addition of methanol (2 mL). Cooling was discontinued and the mixture was allowed to reach ambient temperature. An aqueous solution of Rochelle's salt was added. The biphasic mixture was stirred vigorously for 2 h and the resulting layers were separated. The aqueous layer was extracted once further with hexanes, then with three portions of ethyl acetate. The combined extracts were washed with brine, dried over sodium sulfate, decanted and concentrated to afford the racemic aldehyde product, used without further purification (0.7 g, 97%). $^1$H NMR (400 MHz, CDCl$_3$): δ 9.74 (d, 1H), 4.62 (ddd, 1H), 2.68-2.61 (m, 1H), 2.22-2.11 (m, 1H), 1.95-1.83 (m, 1H), 1.80-1.57 (m, 4H), 0.85 (s, 9H), 0.05 (s, 3H), 0.04 (s, 3H).

Step 3. (E)- and (Z)-3-((1R,2R)-2-(tert-butyldimethylsilyloxy}cyclopentyl)acrylonitrile and (E)- and (Z)-3-((1S,2S)-2-(tert-butyldimethylsilyloxy}cyclopentyl)acrylonitrile

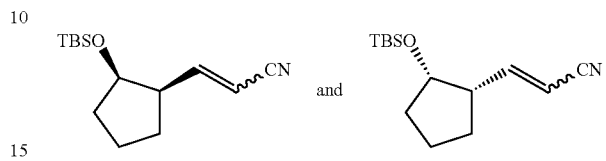

To a solution of (1S,2R)-2-(tert-butyldimethylsilyloxy)cyclopentanecarbaldehyde and (1R,2S)-2-(tert-butyldimethylsilyloxy)cyclopentanecarbaldehyde (0.36 g, 1.6 mmol, from Step 2) in toluene (9 mL) was added (triphenylphosphoranylidene)acetonitrile (0.475 g, 1.58 mmol) and the reaction was heated to 80° C. for 2 h. The reaction was cooled to room temperature and water was added. The product was extracted with three portions of ethyl ether. The extracts were washed with brine, dried over sodium sulfate, decanted and concentrated to provide the racemic mixture of E- and Z-olefin isomers which was used without further purification. $^1$H NMR (400 MHz, CDCl$_3$): δ 6.82 (dd, 1H, trans olefin), 6.63 (dd, 1H, cis olefin), 5.307 (dd, 1H, trans olefin), 5.305 (dd, 1H, cis olefin), 4.24 (ddd, 1H), 4.20 (ddd, 1H), 2.96-2.86 (m, 1H), 2.53-2.43 (m, 1H), 1.95-1.56 (m, 12H), 0.87 (s, 9H), 0.86 (s, 9H), 0.04-0.01 (singlets, together 12H).

Step 4. (3R)- and (3S)-3-[(1R,2R)-2-hydroxycyclopentyl]-3-[4-(7H-pyrrolo[2,3-d]-pyrimidin-4-yl)-1H-pyrazol-1-yl]propanenitrile and (3R)- and (3S)-3-[(1S,2S)-2-hydroxycyclopentyl]-3-[4-(7H-pyrrolo[2,3-d]pyrimidin-4-yl)-1H-pyrazol-1-yl]propanenitrile To a solution of (E)- and (Z)-3-((1R,2R)-2-(tert-butyldimethylsilyloxy)cyclopentyl)acrylonitrile and (E)- and (Z)-3-((1S,2S)-2-(tert-butyldimethylsilyloxy)cyclopentyl)acrylonitrile (0.40 g, 1.6 mmol, crude product from Step 3) in acetonitrile (20 mL) was added 4-(1H-pyrazol-4-yl)-7-{[2-(trimethylsilyl)ethoxy]methyl}-7H-pyrrolo[2,3-d]pyrimidine (0.50 g, 1.6 mmol) and 1,8-diazabicyclo[5.4.0]undec-7-ene (DBU, 0.24 mL, 1.6 mmol). The reaction was stirred for 2 h at room temperature, and further DBU (0.24 mL, 1.6 mmol) was added. The reaction was stirred for 3 days and was concentrated. Flash column chromatography (eluting with a gradient from 10-40% ethyl acetate/hexanes) was used to purify product which was then treated with 20% TFA in DCM for 3 h, evaporated, and treated with excess ethylenediamine in methanol solution overnight. When removal of SEM protecting group was complete, any remaining TBS protecting group was removed by stirring with EtOH/H$_2$O/c.HCl for 3 hours (10:4:3 volume ratio). The fully deprotected products were purified by preparative HPLC-MS (0.15% NH$_4$OH in a gradient of MeCN/H$_2$O). All fractions of M+H=323 were pooled and evaporated (approximately 80 mg). The products were subjected to a series of chiral chromatographic purifications as follows: Chiral Technologies Chiralcel OJ-H (3×25 cm, 5 Tm) eluting with 20% EtOH/80% Hexanes at a flow rate of 25 mL/min to afforded Peak 1 (19 mg), the following minor peak not collected; Peak 2 (60 mg), Peak 3 (6 mg). Peak 2 was a mixture which was then further separated using Chiral Technologies Chiralpak IA (2×25 cm, 5 Tm) eluting with a gradient of 70% EtOH/30% Hexanes at a flow rate of 8 mL/min into three components. These were labeled Peak 2-1 (run 2, peak 1, 32 mg) which was a mixture of products, Peak 2-2 (6.5 mg) and Peak 2-3 (13.7 mg). Peak 2-1 was further separated into three components using Chiral Technologies Chiralpak IA (2×25 cm, 5 Tm) eluting with a gradient of 25% EtOH/75% Hexanes at a flow rate of 12 mL/min. The isolated products were labeled Peak 2-1-1 (10.5 mg); 2-1-2 (13 mg); and 2-1-3 (2.3 mg).

Peak 1: $^1$H NMR (500 MHz, CD$_3$OD): δ 8.65 (s, 1H), 8.62 (s, 1H), 8.37 (s, 1H), 7.49 (d, 1H), 6.95 (d, 1H), 4.71 (ddd, 1H), 4.28 (br t, 1H), 3.26 (dd, 1H), 3.21 (dd, 1H), 2.53-2.45 (m, 1H), 1.98-1.73 (m, 3H), 1.62-1.47 (m, 2H), 1.38-1.29 (m, 1H); LCMS (M+H)$^+$: 323.

Peak 2-1-1: $^1$H NMR (300 MHz, CD$_3$OD): δ 8.64 (s, 1H), 8.59 (s, 1H), 8.38 (s, 1H), 7.49 (d, 1H), 6.94 (d, 1H), 4.90-4.78 (m, 1H), 3.64 (br t, 1H), 3.21 (dd, 1H), 3.07 (dd, 1H), 2.55-2.40 (m, 1H), 2.01-1.58 (m, 6H); LCMS (M+H)$^+$: 323.

Peak 2-1-2: $^1$H NMR (500 MHz, CD$_3$OD): δ 8.65 (s, 1H), 8.62 (s, 1H), 8.37 (s, 1H), 7.49 (d, 1H), 6.95 (d, 1H), 4.71 (ddd, 1H), 4.28 (br t, 1H), 3.26 (dd, 1H), 3.21 (dd, 1H), 2.53-2.45 (m, 1H), 1.98-1.73 (m, 3H), 1.62-1.48 (m, 2H), 1.38-1.26 (m, 1H); LCMS (M+H)$^+$: 323.

Peak 2-3: $^1$H NMR (300 MHz, CD$_3$OD): δ 8.64 (s, 1H), 8.59 (s, 1H), 8.38 (s, 1H), 7.48 (d, 1H), 6.93 (d, 1H), 4.90-4.78 (m, 1H), 3.64 (br t, 1H), 3.21 (dd, 1H), 3.07 (dd, 1H), 2.55-2.40 (m, 1H), 2.01-1.58 (m, 6H); LCMS (M+H)$^+$: 323.

Example 3

Racemic 3-(1-Hydroxycyclopentyl)-3-[4-(7H-pyrrolo[2,3-d]pyrimidin-4-yl)-1H-pyrazol-1-yl]propanenitrile trifluoroacetate salt

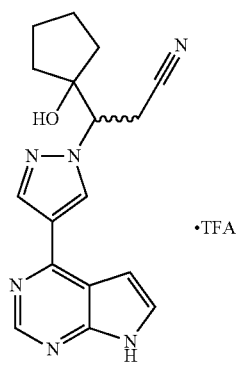

Step 1.
1-[(trimethylsilyl)oxy]cyclopentanecarbaldehyde

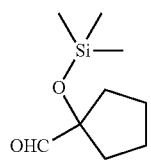

The reaction was carried out in a procedure similar to that described in Tetrahedron, 50(9), 2821-30; 1994: To a solution of 1-[(trimethylsilyl)oxy]cyclopentanecarbonitrile (2.25 g, 12.3 mmol, prepared as described in Organometallics, 3(11), 1660-5; 1984) in toluene (18 mL) at −45° C. was added dropwise 1.0 M of diisobutylaluminum hydride in hexane (17.2 mL, 17.2 mmol). The solution was then allowed to warm to 0° C. and stir for 1 h at this temperature. The reaction mixture was poured into a mixture of diethyl ether (25 mL) and ammonium chloride (25 mL, saturated). To the resulting mixture, at 15° C., was added a dilute solution of sulfuric acid (prepared by diluting 1.53 mL of concentrated H$_2$SO$_4$ with 50 mL water). The solution was then stirred at a temperature of 5° C. overnight. The mixture was extracted with three portions of diethyl ether, the combined extracts were washed with brine, dried over sodium sulfate, decanted and concentrated to afford product (0.84 g, 36%), which was used without further purification in Step 2. $^1$H NMR (300 MHz, CDCl$_3$): δ 9.47 (s, 1H), 1.88-1.46 (m, 8H), 0.00 (s, 9H).

Step 2. (2E)- and (2Z)-3-{1-[(trimethylsilyl)oxy]cyclopentyl}acrylonitrile

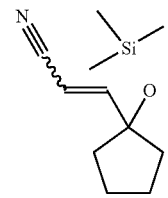

Diethyl cyanomethylphosphonate (0.912 mL, 5.64 mmol) was added dropwise to a suspension of sodium hydride (0.198 g, 4.96 mmol) in tetrahydrofuran (10 mL) at 0° C. Following addition, the reaction was warmed to room temperature and stirred for 45 minutes. The mixture was recooled to 0° C. and 1-[(trimethylsilyl)oxy]cyclopentanecarbaldehyde (0.84 g, 4.5 mmol) in tetrahydrofuran (20 mL) was introduced. The reaction was allowed to warm to room temperature and stir for 2 hours. Water and ethyl acetate were added into the reaction and the layers separated. The aqueous layer was extracted with two further portions of ethyl acetate. The combined organic extracts were washed with brine, dried over sodium sulfate, decanted and concentrated to afford product as a mixture of olefin isomers, used without further purification in Step 3. $^1$H NMR (300 MHz, CDCl$_3$): δ 6.80 (d, 1H, trans/major product), 6.53 (d, 1H, cis/minor product), 5.52 (d, 1H, trans), 5.28 (d, 1H, cis), 2.06-0.76 (m, 16H total for both isomers), 0.18 (s, 9H, minor product), 0.13 (s, 9H, major product).

Step 3. racemic 3-(1-hydroxycyclopentyl)-3-(4-(7-((2-(trimethylsilyl)ethoxy)methyl)-7H-pyrrolo[2,3-d]pyrimidin-4-yl)-1H-pyrazol-1-yl)propanenitrile

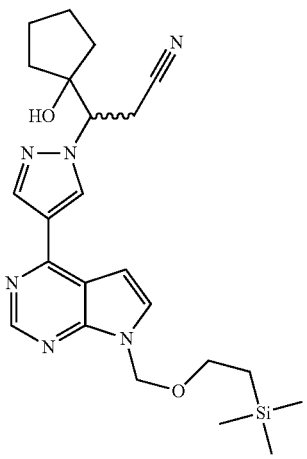 [SMILES: C[Si](C)(C)CCOCn1ccc2c(-c3cnn(C(CC#N)C4(O)CCCC4)c3)ncnc21]

To a suspension of (2E)- and (2Z)-3-{1-[(trimethylsilyl)oxy]cyclopentyl}acrylonitrile (0.94 g, 4.5 mmol) and 4-(1H-pyrazol-4-yl)-7-{[2-(trimethylsilyl)ethoxy]methyl}-7H-pyrrolo[2,3-d]pyrimidine (1.4 g, 4.5 mmol) in acetonitrile (20 mL) was added 1,8-diazabicyclo[5.4.0]undec-7-ene (0.67 mL, 4.5 mmol). The reaction was allowed to stir at room temperature for 6 days. The acetonitrile was evaporated. The desired unprotected alcohol product was isolated from the mixture of unprotected alcohol and TMS-protected alcohol products using flash column chromatography, eluting with a gradient from 0-80% ethyl acetate in hexanes (890 mg, 44%). $^1$H NMR (300 MHz, CDCl$_3$): δ 8.87 (s, 1H), 8.56 (br s, 1H), 8.35 (s, 1H), 7.46 (d, 1H), 6.84 (d, 1H), 5.69 (s, 2H), 4.40 (dd, 1H), 4.03 (s, 1H), 3.55 (dd, 2H), 3.46 (dd, 1H), 2.97 (dd, 1H), 2.04-1.27 (m, 8H), 0.93 (dd, 2H), −0.05 (s, 9H); LCMS (M+H)$^+$: 453.1.

Step 4. racemic 3-(1-hydroxycyclopentyl)-3-[4-(7H-pyrrolo[2,3-d]pyrimidin-4-yl)-1H-pyrazol-1-yl]propanenitrile trifluoroacetate salt A solution of racemic 3-(1-hydroxycyclopentyl)-3-[4-(7-{[2-(trimethylsilyl)ethoxy]methyl}-7H-pyrrolo[2,3-d]pyrimidin-4-yl)-1H-pyrazol-1-yl]propanenitrile (0.100 g, 0.221 mmol) in methylene chloride (4 mL) and trifluoroacetic acid (1 mL) was stirred for 2 hours and the solvents were evaporated. The residue was stirred with ethylenediamine (0.1 mL, 2 mmol) in methanol (4.5 mL) for 1 hour and evaporated. The crude product was reconstituted in methanol and purified by two successive chromatographic steps using preparative HPLC-MS (eluting with a gradient of acetonitrile/H$_2$O containing 0.15% NH$_4$OH for the first run, followed by a gradient of acetonitrile/H$_2$O containing 0.1% TFA for the second run) to afford the racemic product as the trifluoroacetate salt. $^1$H NMR (400 MHz, d$_6$-dmso): δ 12.72 (br s, 1H), 8.94 (s, 1H), 8.86 (s, 1H), 8.49 (s, 1H), 7.82 (s, 1H), 7.21 (s, 1H), 4.80 (dd, 1H), 3.51 (dd, 1H), 3.22 (dd, 1H), 1.79-1.42 (m, 7H), 1.25-1.15 (m, 1H); LCMS (M+H)$^+$: 323.1.

Example A

Metabolites 1-39 were isolated from human, rat or dog urine, plasma, or feces after administration of Compound I in connection with pharmacokinetic and toxicokinetic studies. The identity of the metabolites were determined after isolation of the metabolite using HPLC methods. The method used and the corresponding retention times of the metabolites are presented in Table 2. Tandem MS/MS analysis and higher order MS$^n$ experiments were conducted as required to elucidate structural information.

Compound I demonstrates a protonated molecular ion at m/z 307, and a product ion spectrum showing signals at m/z 266, 186, and 159. The fragment ion at m/z 266 is consistent with the loss of the carbonitrile moiety. The diagnostic fragment ion at m/z 186 is indicative of the loss of the intact cyclopentylpropanenitrile moiety. The fragment ion at m/z 159 indicates the loss of the cyclopentylpropanenitrile in conjunction with cleavage through the pyrazole ring of Compound I.

Metabolite compounds 1, 2, 27, and 29 were observed primarily in urine from human subjects, with trace levels of compounds 27 and 29 observed in plasma. Full scan mass spectrometry demonstrated a protonated molecular ion at m/z 339, consistent with bis-hydroxylation of Compound I. Product ion fragmentation of these m/z 339 ions yields virtually identical spectra for these metabolites, with ions observed at m/z 321, 186, 159 and 154. The ion at m/z 321 is consistent with a water loss and suggests that at least one hydroxylation may be on the cyclopentyl ring. The ions at m/z 186 and m/z 159 are consistent with an intact pyrazole-pyrrolopyrimidine. The ion at m/z 154 is consistent with a neutral loss of the entire unmodified pyrazole/pyrrolopyrimidine moiety. Minor fragment ions at m/z 298 and m/z 280 suggest the loss of the elements of acetonitrile, with and without the facile water loss, further restricting the location of the hydroxylations to the cyclopentyl moiety. This is further supported by the ion at m/z 237, which is consistent with the loss of the modified cyclopentyl, leaving the rest of the molecule unmodified.

Compound 31 was found in urine from human subjects. Full scan mass spectrometry demonstrated a protonated molecular ion at m/z 339, consistent with the addition of 32 amu to Compound I. Product ion fragmentation of the m/z 339 ion yields fragment ions at m/z 311, 218, and 191. The primary fragment at m/z 218 which is consistent with the addition of 32 amu to the pyrazole-pyrrolopyrimidine moiety. The fragment ion at m/z 191 is consistent with a loss of CHN from the pyrazole moiety of the putative bis hydroxylated pyrazole-pyrrolopyrimidine, restricting the location of the modification(s) to the pyrrolopyrimidine. The fragment ion at m/z 311 likely arises from initial cleavage of the amide bond, followed by the loss of CO from the pyrrolidinone. Structural assignment of Compound 31 using mass spectrometry alone led to an ambiguous result, therefore Compound 31 was isolated from human urine and analyzed by $^1$H and $^{13}$C NMR. The structure of 31 is identified as an amide-alcohol metabolite of the saturated pyrrolopyrimidine moiety of Compound I. The proton NMR spectrum of 31 has a singlet at δ 3.56 with an intensity of 2H. This singlet has a long range correlation to a carbon at δ 177.9, consistent with an amide. In addition, a nuclear Overhauser enhancement (nOe) occurs between H3 and H9.

Compound 32 was found in plasma and urine from human subjects. Full scan mass spectrometry demonstrated a protonated molecular ion at m/z 339, consistent with the addition of 32 amu to Compound I. Product ion fragmentation of the m/z 339 ion yields fragment ions at m/z 218, and 191. The primary fragment at m/z 218 which is consistent with the addition of 32 amu to the pyrazole-pyrrolopyrimidine moiety. The fragment ion at m/z 191 is consistent with a loss of CHN from the pyrazole moiety of the putative bis hydroxylated pyrazole-pyrrolopyrimidine, restricting the location of the modification(s) to the pyrrolopyrimidine. Structural assignment of Compound 32 using mass spectrometry alone led to an ambiguous result, therefore Compound 32 was isolated from human urine and analyzed by $^1$H and $^{13}$C NMR. The structure of Compound 32 is identified as a keto-alcohol metabolite of the saturated pyrrolopyrimidine moiety of Compound I. The proton NMR spectrum of 32 has a singlet at δ 3.82 which has an intensity of 2H and shows a long range correlation to at carbon at δ 191.5, consistent with a ketone. There was no nuclear Overhauser enhancement (nOe) observed from H2 to any other proton.

Compound 40 was observed in plasma and urine from human subjects. Full scan mass spectrometry demonstrated a protonated molecular ion at m/z 341, consistent with the addition of 34 amu to Compound I. Product ion fragmentation of the m/z 341 ion yields fragment ions at m/z 323, 220, 202, and 175. The fragment ion at m/z 323 arises from the loss of water from the pyrrolidine diol. Fragment ions at m/z 220 and 202 are consistent with a doubly hydroxylated saturated pyrrolopyrimidine, with and without the observed facile water loss. The ion observed at m/z 175 is consistent with loss of CHN from the pyrazole moiety of the doubly hydroxylated saturated pyrazole pyrrolopyrimidine following the facile water loss. Compound 40 is identified as 3-cyclopentyl-3-(4-(5,6-dihydroxy-6,7-dihydro-5H-pyrrolo[2,3-d]pyrimidin-4-yl)-1H-pyrazol-1-yl)propanenitrile.

Conjugates of singly hydroxylated metabolites of Compound I having an observed m/z of 499 were observed in urine from human, with two of the seven conjugates also observed in trace amounts in human plasma. Initial product ion fragmentation yields virtually identical spectra for six of these metabolites, with an observed ion at m/z 323, consistent with the loss of the glucuronide conjugate. The product ion fragmentation (MS$^3$) of these m/z 323 fragment ions again demonstrated virtually identical mass spectra, with fragment ions at m/z 305, 186, and 159. The fragment ion found at m/z 305 is consistent with a loss of water (18 amu), suggesting hydroxylation and subsequent collision induced fragmentation on a saturated portion of the molecule, restricting the site of modification to the cyclopentyl moiety. The fragment ions at m/z 186 and m/z 159 are consistent with an unmodified pyrazole-pyrrolopyrimidine. Additional minor fragment ions were too weak to assign them with any certainty. The identity of these putative metabolites was confirmed by hydrolysis of the isolated glucuronide conjugates with β-Glucuronidase to reveal the aglycone, which was then subject to analysis by HPLC-MS where the retention times and mass spectra of the liberated aglycones were matched with those of singly hydroxylated metabolite standards. The aglycones of these glucuronide conjugate metabolites correspond to 2-hydroxyl metabolites (Metabolite 9, Table 1) and 3-hydroxyl metabolites (Metabolite 8, Table 1). The aglycone of the seventh glucuronide conjugate metabolite, compound 42, corresponds to a singly hydroxylated metabolite of the pyrazole-pyrrolopyrimidine moiety of Compound I, which was not independently observed in plasma or urine from human subjects. Full scan mass spectrometry demonstrated a protonated molecular ion at m/z 323, consistent with the addition of 16 amu to Compound I. Product ion fragmentation of the m/z 323 ion yields a primary fragment at m/z 202 which is consistent with the addition of 16 amu to the pyrazole-pyrrolopyrimidine moiety. The fragment ion at m/z 175 is consistent with a loss of CHN from the pyrazole moiety of the putative hydroxylated pyrazole-pyrrolopyrimidine, restricting the location of the modification to the pyrrolopyrimidine. The structure of metabolite compound 42 is identified as a glucuronide conjugate of a singly hydroxylated pyrrolopyrimidine moiety of Compound I.

Metabolite compound 41 was found in urine from human subjects. Full scan mass spectrometry indicated a protonated molecular ion at m/z 583, consistent with glucuronide conjugation of unmodified Compound I. Product ion fragmentation of the m/z 583 ion yields a primary fragment at m/z 307 which is consistent with the loss of an intact glucuronide. Minor fragment ions at m/z 186 and m/z 159 are consistent with those observed for Compound I. MS$^3$ fragmentation of the m/z 307 fragment ion also revealed fragment ions at m/z 186 and m/z 159. Compound 41 is identified as an N-linked glucuronide conjugate of Compound I.

TABLE 2

| Compound | m/z | Analysis method | Retention time (min) | Metabolite description |
|---|---|---|---|---|
| 1 | 339 | A4 | 4.3 | Di-hydroxylation of cyclopentyl moiety |
| 2 | 339 | A4 | 4.8 | Di-hydroxylation of cyclopentyl moiety |
| 3 | 499 | A3 | 4.8 | 6-(3-(1-(4-(7H-pyrrolo[2,3-d]pyrimidin-4-yl)-1H-pyrazol-1-yl)-2-cyanoethyl)cyclopentyloxy)-3,4,5-trihydroxytetrahydro-2H-pyran-2-carboxylic acid |
| 4 | 499 | A3 | 5.3 | O-glucuronidation of cyclopentyl moiety |
| 5 | 499 | A3 | 5.8 | O-glucuronidation of cyclopentyl moiety |
| 6 | 339 | A4 | 5.9 | Dihydroxylation |
| 7 | 499 | A3 | 6.3 | O-glucuronidation of cyclopentyl moiety |
| 8 | 499 | A3 | 6.8 | 6-(3-(1-(4-(7H-pyrrolo[2,3-d]pyrimidin-4-yl)-1H-pyrazol-1-yl)-2-cyanoethyl)cyclopentyloxy)-3,4,5-trihydroxytetrahydro-2H-pyran-2-carboxylic acid |
| 9 | 339 | A4 | 8.1 | Hydroxylation on cyclopentyl and pyrazole or pyrrolopyrimidine moieties |
| 10 | 339 | A4 | 8.4 | Hydroxylation on cyclopentyl and pyrazole or pyrrolopyrimidine moieties |
| 11 | 355 | A1 | 8.5 | Tri-hydroxylation of cyclopentylpropanenitrile moiety |
| 12 | 355 | A1 | 14.6 | Tri-hydroxylation of cyclopentylpropanenitrile moiety |
| 13 | 499 | A1/A3 | 15.3 | O-glucuronidation of cyclopentylpropanenitrile moiety |
| 14 | 499 | A1/A3 | 18.6 | O-glucuronidation of cyclopentylpropanenitrile moiety |
| 15 | 499 | A1/A3 | 25.3 | O-glucuronidation of cyclopentylpropanenitrile moiety |
| 16 | 321 | A1/A3 | 26.5 | ketone on cyclopentylpropanenitrile moiety |
| 17 | 339 | A1 | 28 | Hydroxylation on cyclopentylpropanenitrile and pyrrolidine moieties |
| 18 | 323 | A1/A3 | 35 | Hydroxylation of the cyclopentylpropanenitrile moiety |
| 19 | 499 | A1/A3 | 42.2 | O-glucuronidation of cyclopentylpropanenitrile moiety |
| 20 | 355 | A1 | 44.2 | Di-hydroxylation of cyclopentylpropanenitrile moiety and hydroxylation of pyrrolidine moiety |
| 21 | 355 | A1 | 51.4 | Di-hydroxylation of cyclopentylpropanenitrile moiety and hydroxylation of pyrrolidine moiety |
| 22 | 339 | A1 | 52.2 | Hydroxylation on cyclopentylpropanenitrile and pyrrolidine moieties |
| 23 | 339 | A1 | 55.8 | Hydroxylation on cyclopentylpropanenitrile and pyrrolidine moieties |
| 24 | 355 | A1 | 4.7 | Dihydroxylation on cyclopentylpropanenitrile moiety and hydroxylation of pyrrolidine moiety |
| 25 | 339 | A1 | 7.7 | Di-hydroxylation on cyclopentylpropanenitrile moiety |
| 26 | 339 | A1 | 8.4 | Di-hydroxylation on cyclopentylpropanenitrile moiety |
| 27 | 339 | A1 | 11.9 | Di-hydroxylation on cyclopentylpropanenitrile moiety |
| 28 | 323 | A1/A3 | 12.4 | Hydroxylation on cyclopentylpropanenitrile moiety |
| 29 | 339 | A1 | 12.7 | Di-hydroxylation of cyclopentylpropanenitrile moiety |
| 30 | 515 | A3 | 9.6 | Di-hydroxylation of cyclopentylpropanenitrile moiety and O-glucuronidation |
| 31 | 339 | A3 | 27 | 3-cyclopentyl-3-(4-(2,6-dioxo-3,5,6,7-tetrahydro-2H-pyrrolo[2,3-d]pyrimidin-4-yl)-1H-pyrazol-1-yl)propanenitrile |

TABLE 2-continued

| Compound | m/z | Analysis method | Retention time (min) | Metabolite description |
|---|---|---|---|---|
| 32 | 339 | A3 | 29 | 3-cyclopentyl-3-(4-(2-hydroxy-5-oxo-6,7-dihydro-5H-pyrrolo[2,3-d]pyrimidin-4-yl)-1H-pyrazol-1-yl)propanenitrile |
| 33 | 323 | A1 | 55.8 | Hydroxylation of pyrrolopyrimidine moiety |
| 34 | 499 | A1/A3 | 37.5 | O-glucuronidation of cyclopentylpropanenitrile moiety |
| 35 | 339 | A6 | 5.1 | 3-(4-(7H-pyrrolo[2,3-d]pyrimidin-4-yl)-1H-pyrazol-1-yl)-3-(1,2-dihydroxycyclopentyl)propanenitrile |
| 36 | 323 | — | — | 3-(4-(7H-pyrrolo[2,3-d]pyrimidin-4-yl)-1H-pyrazol-1-yl)-3-(1-hydroxycyclopentyl)propanenitrile |
| 37 | 323 | A6 | 8.1 | 3-cyclopentyl-3-(4-(6-oxo-6,7-dihydro-5H-pyrrolo[2,3-d]-pyrimidin-4-yl)-1H-pyrazol-1-yl)propanenitrile |
| 38 | 339 | A6 | 5.4 | 3-(3-hydroxycyclopentyl)-3-(4-(6-oxo-6,7-dihydro-5H-pyrrolo[2,3-d]pyrimidin-4-yl)-1H-pyrazol-1-yl)propanenitrile |
| 39 | 371 | A3 | 17.7 | quadrupole hydroxylation |
| 40 | 341 | A7 | 27.7 | 3-cyclopentyl-3-(4-(5,6-dihydroxy-6,7-dihydro-5H-pyrrolo[2,3-d]pyrimidin-4-yl)-1H-pyrazol-1-yl)propanenitrile |
| 41 | 483 | A7 | 36.0 | 6-(4-(l-(2-cyano-1-cyclopentylethyl)-1H-pyrazol-4-yl)-7H-pyrrolo[2,3-d]-pyrimidin-7-yl)-3,4,5-trihydroxytetrahydro-2H-pyran-2-carboxylic acid |
| 42 | 499 | A7 | 37.7 | Hydroxylation of pyrrolopyrimidine moiety and O-glucuronidation |

Method A1: Biotransformation of $^{14}$C-Compound I in Human, Dog, and Mouse Plasma, Urine, and Fecal Samples Sample Preparation for Metabolite Profiling:

Plasma:

Plasma samples from all subjects were pooled by subject and/or by time point. The pooled plasma samples were prepared for HPLC-Radiometric analysis as follows: Aliquots of the pooled plasma samples were initially extracted with approximately two equivalent (W/V) volumes of 1% formic acid in HPLC-grade acetonitrile, followed by vigorous vortexing, and centrifugation to remove denatured plasma proteins. The supernatant was reserved and passed through a pre-conditioned Waters C-18 Solid phase extraction cartridge, and the filtrate retained. The SPE cartridge was retained. The remaining plasma pellet was then extracted three times with 1% formic acid in HPLC-grade acetonitrile/water (90/10), with centrifugation after each extraction. All supernatants were reserved. Each formic acid/acetonitrile/water extraction supernatant was used to elute the SPE cartridge. The SPE cartridge was then rinsed with 1% formic acid in methanol. All eluants were retained, combined, and evaporated under a stream of nitrogen at 30° C. The remainder of this extraction was reconstituted in approximately 0.6 ml of 0.1% formic acid in water, vortexed and centrifuged to remove particulate matter. The supernatant was then analyzed by HPLC-Flow Radiometry and HPLC-MS.

Urine:

Aliquots of approximately equal amounts of urine from each of the subjects were pooled to represent appropriate time intervals post-dose. Prior to HPLC-Radiometric analysis, each pooled urine sample was centrifuged at 4,000 rpm for 10 min to remove particulate matter, then analyzed directly.

Feces:

Aliquots of fecal homogenates from each subject were pooled to represent appropriate time intervals post-dose. The pooled fecal homogenate samples were prepared for HPLC-Radiometric analysis as follows:

Aliquots of approximately 5 grams of fecal homogenate were initially extracted with approximately two equivalent (W/V) volumes of Millipore water, followed by centrifugation to remove solids. The supernatant was reserved and passed through a pre-conditioned Waters C-18 Solid phase extraction cartridge. The SPE cartridge was retained. The remaining fecal pellet was then extracted three times with 1% formic acid in HPLC-grade acetonitrile/water (90/10), with centrifugation after each extraction. All supernatants were reserved. Each formic acid/acetonitrile/water extraction supernatant was used to elute the SPE cartridge. All eluants were retained, combined, and evaporated under a stream of nitrogen at 30° C. The remainder of this extraction was reconstituted in approximately 2.0 ml of 0.1% formic acid in water, vortexed and centrifuged to remove particulate matter. The supernatant was then analyzed by HPLC-Flow Radiometry and HPLC-MS HPLC-Flow Radiometry Analytical Method:

All samples were analyzed by either HPLC-Flow radiometry or HPLC-MS using analytical systems that were as identical as practicable. The HPLC-Flow Radiometry system consisted of an Agilent HP1100 series Quaternary pump, Autosampler, and UV detector interfaced with a Raytest Ramona-90 flow scintillation detector with a 500 µL liquid scintillation cell. Separation of Compound I and its metabolites was achieved with a Waters Symmetry C-18 HPLC column, 4.6×250 mm, 5 µm particle size HPLC column. Mobile phase "A" consisted of 0.1% formic acid in HPLC-grade water, with mobile phase "B" consisting of HPLC-grade methanol/acetonitrile (1:1). Elution of analytes was achieved through use of a linear increasing gradient of mobile phase "B". Two different gradient elution methods were employed at various times as needed. Chromatographic conditions for these two methods are outlined below in Tables 3 and 4.

HPLC-Mass Spectrometry Analytical Method:

The HPLC-Flow Radiometry system consisted of an Agilent HP1100 series Quaternary pump, and Leap Technologies CTC-PAL Autosampler interfaced with an Applied Biosystems API 4000 Qtrap operated in positive ion detection mode. Full scan (MS) and data dependent product ion scans (MS$^2$) were employed in the characterization of metabolites of Compound I. Select MRM transitions were also used to scan for and identify previously identified and characterized metabolites. Separation of Compound I and its metabolites was achieved with a Waters Symmetry C-18 HPLC column, 4.6×250 min, 5 µm particle size HPLC column. Mobile phase "A" consisted of 0.1% formic acid in HPLC-grade water, with mobile phase "B" consisting of HPLC-grade methanol/acetonitrile (1:1). Elution of analytes was achieved through use of a linear increasing gradient of mobile phase "B". Two different gradient elution methods were employed at various times as needed. Chromatographic conditions for these two methods are outlined below in Tables 3 and 4.

TABLE 3

Chromatographic Conditions

| Time (min) | % B | Flow (µl/min) |
|---|---|---|
| 0.0 | 10 | 1000 |
| 45.0 | 20 | 1000 |

TABLE 3-continued

| Chromatographic Conditions | | |
|---|---|---|
| Time (min) | % B | Flow (µl/min) |
| 50.0 | 50 | 1000 |
| 55.0 | 90 | 1000 |
| 57.0 | 90 | 1000 |
| 57.1 | 10 | 1000 |
| 65.0 | 10 | 1000 |

TABLE 4

| Chromatographic Conditions | | |
|---|---|---|
| Time (min) | % B | Flow (µl/min) |
| 0.0 | 10 | 1000 |
| 45.0 | 20 | 1000 |
| 90.0 | 40 | 1000 |
| 92.0 | 90 | 1000 |
| 97.0 | 90 | 1000 |
| 97.1 | 10 | 1000 |
| 102.0 | 10 | 1000 |

Method A2: Biotransformation of Compound I: Isolation of Metabolites Isolation of Metabolites from Human Urine:

Solid phase extraction using 20 cc Waters HLB SPE cartridges (1 gram sorbent) were used to concentrate metabolites of Compound I from pooled urine samples. The cartridges were conditioned first with 100% HPLC grade methanol, then with Millipore water. The cartridge was then immediately loaded with up to 10 ml of raw unprocessed urine. The cartridge was the sequentially eluted using several concentrations of HPLC grade methanol in water (Table 5).

TABLE 5

| Operation | Solvent Composition | Volume |
|---|---|---|
| Condition | 100% Methanol | 10 ml |
| Condition | 100% Millipore Water | 10 ml |
| Load | Urine | 7-10 ml |
| Elute | 5% Methanol in Water | 10 ml |
| Elute | 25% Methanol in Water | 10 ml |
| Elute | 50% Methanol in Water | 10 ml |
| Elute | 75% Methanol in Water | 10 ml |
| Elute | 100% Methanol in Water | 10 ml |

Aliquots of the initial urine, the last load volume, and every wash/elution volume were analyzed by LC-MS for the presence of Compound I and metabolites of interest. There were no significant amounts of either Compound I, or its metabolites in any of the load volumes, or washes/elutions up to 25% methanol in Millipore water. No significant amounts of drug or metabolites were found in the 100% methanol elution aliquots. Elution volumes from the 50% and 75% methanol elutions were each reduced in volume using the Genevac centrifugal evaporator and reconstituted to a final volume of ~2 mL before being serially injected onto the LC-MS for fraction collection of the metabolites of interest.

Analytical Conditions:

Samples were analyzed by LC-MS using a Finnigan LCQ Deca XP Plus interfaced with a Shimadzu Binary HPLC stack consisting of a Sil-HTC Autosampler and system controller, and two Sil 10ADVp high pressure LC pumps. The mass spec was operated in positive ion detection mode, using data dependent scanning to yield. MS and data-dependent $MS^2$ data. A Shimadzu UV detector, Sil SPD10 AVp was used at a detection wavelength of 254 nm to monitor the HPLC eluant in concert with the mass spectrometer.

Mobile phase "A" consisted of 5 mM ammonium formate which was pH adjusted to pH 3.2 with formic acid (approximately 0.1% by volume). Mobile phase "B" consisted of 90% acetonitrile/10% methanol. The HPLC column used was a Zobax XDB C-18, 3.0 mm×150 mm, 5.0 Tm particle size. Elution of analyte was through use of a linearly increasing gradient of mobile phase "B". Chromatographic conditions for the analytical scale analysis are outlined in Table 6 below.

TABLE 6

| Chromatographic Conditions | | |
|---|---|---|
| Time (min) | % B | Flow (Tl/min) |
| 0.0 | 10 | 300 |
| 1.0 | 10 | 300 |
| 45.0 | 40 | 300 |
| 50.0 | 90 | 300 |
| 54.0 | 90 | 300 |
| 54.1 | 10 | 300 |
| 60.0 | 10 | 300 |

Semi-PREP Analytical Conditions.

Samples were analyzed by LC-MS as above with the following changes:
The HPLC column used was a Phenomenex Polar RP 10 mm×150 mm 5 Tm particle size.
The initial fractionation was carried out using neutral ammonium acetate as the "A" phase, with a second cleanup step of individual collected peaks carried out using 0.025% formic acid in water as the "A" phase. Mobile phase "B" consisted of 90% acetonitrile/10% methanol.

Initial elution of analytes and automated fraction collection was through use of a linearly increasing gradient of mobile phase "B". Chromatographic conditions for the initial semi preparative analysis are outlined in Table 7 below, but % B was optimized as needed for each individual metabolite in the second cleanup step.

TABLE 7

| Semi-Prep Chromatographic Conditions | | |
|---|---|---|
| Time (min) | % B | Flow (ml/min) |
| 0.0 | 7 | 1.75 |
| 1.0 | 25* | 1.75 |
| 24.0 | 35* | 1.75 |
| 24.1 | 90 | 1.75 |
| 28.0 | 90 | 1.75 |
| 28.1 | 7 | 1.75 |
| 35.0 | 7 | 1.75 |

*Optimized for each individual metabolite in second fractionation step

The eluant stream of the semi-prep analyses were split using a PEEK tee and tubing, with ~1.65 ml/min of the eluant stream being utilized for fraction collection, and the remainder going to the mass spectrometer. The eluant stream composition was monitored by MS and selected MS-MS experiments. Fractions containing the analyte of interest were collected automatically by utilizing the divert valve in concert with a fraction collector.

Method A3: Biotransformation of Compound I in Human and Rat Plasma and Urine Samples
Sample Preparation:

Plasma and urine samples from animal and human subjects which had been orally dosed with Compound I were obtained following single dose and/or multiple dose studies. Residual plasma samples for each subject were pooled by time-weighted-average pooling. Aliquots of the pooled plasma samples (150 μL) were precipitated with two volumes of acetonitrile, vortex mixed and then centrifuged. The supernatants were removed and used for analysis by LC-MS. For human, the urine samples from each individual in the study were pooled to represent 0-12 hours on Day 1 (single dose study) and Day 10 (multiple dose study) of the clinical study. Urine samples were centrifuged at ~15000×g for 10 minutes before analysis and injected directly.

Sample Analysis:

Samples were assayed using electrospray ionization LC-MS with a Thermo Finnigan LCQ Deca-XP Plus Ion-Trap Mass Spectrometer (Thermo-Fisher Scientific Waltham Mass., USA), operated in positive ionization mode. Data dependent scanning was used to generate initial MS to $MS^2$ data. Higher order $MS^n$ experiments were conducted as required to elucidate structural information. The mass spectrometer was coupled to a Shimadzu Sil HT-C combined autosampler/controller combined with a Shimadzu LC-10A binary gradient pump system (Shimadzu Scientific Instruments, Columbia, Md., USA). Gradient conditions are described in Table 8. Separation of Compound I and its metabolites was achieved using a Zorbax XDB C-18 HPLC column (3.0×150 min, 3.5 μm) (Agilent, Santa Clara, Calif. USA) with a mobile phase flow rate of 300 μL/min. Mobile phase "A" consisted of 5 mM ammonium formate in Millipore water which had been pH adjusted to pH 3.2 with formic acid. Mobile phase "B" consisted of 90% acetonitrile/10% methanol.

TABLE 8

HPLC Gradient Elution Scheme

| Time | % Mobile Phase B |
|---|---|
| 0.0 | 10 |
| 1.0 | 10 |
| 45.0 | 40 |
| 50.0 | 90 |
| 54.0 | 90 |
| 54.1 | 10 |
| 60.0 | 10 |

Method A4: Method for Metabolite Characterization of Rat Bile, Plasma and Urine

Urine, feces, and bile samples from rats administered Compound I were pooled. Approximately 30% of each sample was pooled from each time point such that 90% of the excreted dose from one rat was contained in a single sample. Samples from each rat were analyzed separately. Feces samples were extracted using acetonitrile and extraction recovery determined by liquid scintillation counting (LSC) of the extract and combustion and LSC of the unextracted pellet. When available, metabolite standards were used to confirm structures. Peaks accounting for <5% of the administered dose were not reported unless noted otherwise.

Urine, feces, bile and/or plasma samples were analyzed by HPLC and mass spectroscopy to determine the molecular weight of any radioactively labeled metabolites and obtain structural information of these metabolites.

Method A5: Isolation Method

Urine samples from Compound I pharmacokinetic and toxicokinetic studies were pooled together from individual animals of the same species, i.e. dog or rat. Urine samples were extracted with ethyl acetate at a volume ratio of 1 to 1 three times. The ethyl acetate extraction fractions were pooled and volatiles were removed using a rotavap. The resulting residue was dissolved in acetonitrile:water (1:1 v/v), and the solution was subjected to preparative HPLC purification. Isolation of each metabolite was achieved by using the three HPLC conditions below in sequential order.

The concentrated extract was purified by using a mobile phase consisting of 0.1% TFA in water (Solvent A) and 0.1% TFA in acetonitrile (Solvent B), on a Zobax SB C18 column (19×150 mm, 5 Tm) using a gradient of 5% to 60% solvent B over 20 minutes, and a flow rate of 15 mL/min.

1. The fractions collected from the first HPLC purification was then further purified by using a mobile phase consisting of 0.1% TFA in water (Solvent A) and methanol (Solvent B), on a column Zobax SB C18 column (9.6×150 mm, 5 Tm) using a gradient of 5% to 95% solvent B over 25 minutes, and a flow rate of 4 mL/min.
2. Each fraction collected from the second purification with $[M+H]^+=321$ and 323 was subjected to chiral separation using a mobile phase consisting of 15% ethanol and 85% hexanes or 30% ethanol and 70% hexanes, on a chiral column (ChiralCel OD-H, 20×250 mm, 5 Tm) with a flow rate of 15 mL/min.

Method A6: Analysis Method

The retention times for 35, 37 and 38 were obtained from the HPLC analysis using Zorbax SB C18 column (4.6×150 mm, 80 Å, 3.5 Tin) at a column temperature of 40° C. using a mobile phase consisting of 0.05% TFA in Water (Solvent A) and 0.05% TFA in Acetonitrile (Solvent B) with a flow rate of 1 mL/min using a gradient elution scheme shown in Table 9. An in-line UV detection was performed at 220 nm.

TABLE 9

Gradient Elution Scheme

| Time (min) | % ACN |
|---|---|
| 0 | 5 |
| 15 | 95 |
| 18 | 95 |
| 18.5 | 5 |
| 24 | 5 |

Method A7: Alternate Analysis Method

The retention times for 40, 41 and 42 were obtained from the HPLC analysis using a Waters Atlantis® T-3 HPLC column (4.6×150 mm, 3.5 nm) (Waters Corporation, Milford, Mass., USA) with a mobile phase flow rate of 400 μL/min. Mobile phase "A" consisted of 5 mM ammonium formate in Millipore water which had been pH adjusted to pH 3.2 with formic acid. Mobile phase "B" consisted of 100% methanol. The initial mobile phase condition was 90% mobile phase "A"/10% mobile phase "B" with a step gradient to 27% mobile phase "B" in one minute. The initial gradient then progressed in a linear manner to 52% mobile phase "B" in 57 minutes, followed by a second linear gradient to 95% mobile phase "B" in 10 minutes. A five minute column washout period at 95% mobile phase "B" ensued and was followed by a return to starting conditions and an 8 minute column re-equilibration prior to the next analytical injection. 100% of column eluant was routed through a Shimadzu fixed wavelength UV detector, SPD-10Avp (Shimadzu Scientific Instruments, Columbia, Md., USA) monitoring λ 254 nm. Upon exiting the UV detector, the eluant stream was split using a PEEK tee to allow approximately 100 μl of the eluant to be introduced via electrospray ionization to the mass spectrometer. The electrospray source voltage was set at 4.5 kV, with a capillary temperature of 325° C., sheath and sweep gasses were set at 50 and 30 (arbitrary units), respectively. Initial data dependent MS/MS settings included an isolation width of 2.0 amu and a collision energy setting of 42. All other instrument settings and potentials were optimized to achieve maximum signal to noise ratio for Compound I.

Method A8: Enzymatic Hydrolysis of Glucuronide Metabolites of Compound I.

Isolated glucuronide conjugate metabolites of Compound I were incubated with β-glucuronidase with the reaction proceeding to completion in all cases, yielding the associated aglycone, which was analyzed using the same LC-MS method as described above. The retention times and mass spectra of the liberated aglycones were compared with the retention times and mass spectra of the singly hydroxylated metabolite standards of Compound I to assign the identity of the conjugate.

Example B

Metabolite samples of molecular weight of 323 were presumed to be hydroxyl containing metabolites and were dissolved in 200 μL of $CD_3OD$, obtained from Isotec. Samples of molecular weight 321 were presumed to contain a ketone moiety and were dissolved in 200 μL of $CDCl_3$, obtained from Isotec. Samples which were of a molecular weight other than that described above were dissolved in 200 μL of DMSO-$d_6$, also obtained from Isotec. After dissolution, each sample was placed into a 3 mm NMR tube, obtained from Wilmad Glass. Samples were prepared immediately prior to analysis.

Samples were analyzed using a Varian INOVA NMR spectrometer operating at 500 MHz for $^1$H and 125 MHz for $^{13}$C. A 3 mm triple resonance inverse detection gradient probe was used. The sample was kept at 30° C. during the time that all data acquisition was taking place. The probe was locked and shimmed for each sample. Other NMR experiments were performed to obtain the data necessary to determine the structure.

Compound 31 $^1$H (500 MHz, DMSO-$D_6$): δ 8.58 (s, 1H), 8.23 (s, 1H), 4.47 (td, 1H), 3.56 (s, 2H), 3.18 (dd, 1H), 3.13 (dd, 1H), 2.35 (m, 1H), 1.79 (m, 2H), 1.59-1.39 (m, 4H), 1.29 (m, 2H).

Compound 32 $^1$H (500 MHz, DMSO-$D_6$): δ 9.24 (s, 1H), 8.66 (s, 1H), 4.56 (td, 1H), 3.82 (s, 2H), 3.17 (dd, 1H), 3.11 (dd, 1H), 2.35 (m, 1H), 1.79-1.12 (m, 4H), 1.61-1.45 (m, 4H).

Compound 35 $^1$H (500 MHz, DMSO-$D_6$): δ 12.25 (s, 1H), 8.82 (s, 1H), 8.73 (s, 1H), 8.37 (s, 1H), 7.64 (m, 1H), 7.08 (m, 1H), 4.93 (dd, J=11.6, 3.3, 1H), 3.76 (d, J=4.8, 1H), 3.52 (dd, J=17.2, 11.7, 1H), 3.08 (dd, J=17.4, 3.6), 2.04 (m, 1H), 1.76 (m, 1H), 1.63 (m, 1H), 1.54 (m, 2H), 0.95 (m, 1H).

Compound 37 $^1$H (500 MHz, $CDCl_3$): δ 8.71 (s, 1H), 8.17 (s, 1H), 8.00 (s, 1H), 4.22 (td, J=9.6, 3.7, 1H), 3.71 (s, 2H), 3.09 (dd, J=17.0, 9.1, 1H), 2.91 (dd, J=16.8, 3.7, 1H), 2.55 (m, 1H), 1.94 (m, 1H), 1.80-1.45 (m, 5H), 1.27 (m, 1H), 1.19 (m, 1H).

Compound 38 $^1$H (500 MHz, DMSO-$D_6$): δ 11.35 (s, 1H), 8.60 (s, 1H), 8.54 (s, 1H), 8.09 (s, 1H), 4.55 (td, J=9.8, 3.8, 1H), 4.10 (m, 1H), 3.79 (s, 2H), 3.19 (dd, J=16.9, 9.5, 1H), 3.13 (dd, J=17.5, 4.5, 1H), 2.39 (m, 1H), 2.01 (m, 1H), 1.58 (m, 1H), 1.48-1.07 (m, 4H).

Example C

Activity data for Metabolites 1-39, along with free fraction and intrinsic clearance data, can be compared with that for the parent compound, Compound I. JAK activity assays, free fraction assays, and intrinsic clearance assays are described below. Data points can be obtained for individual stereoisomers of Metabolites 1-39. The metabolites can be potent inhibitors of JAK1, JAK2, and JAK3, like Compound I.

In Vitro JAK Kinase Assay

Compounds described herein herein can be tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag can be expressed using baculovirus in insect cells and purified. The catalytic activity of JAK1, JAK2 or JAK3 can be assayed by measuring the phosphorylation of a biotinylated peptide. The phosphorylated peptide can be detected by homogenous time resolved fluorescence (HTRF). $IC_{50}$s of compounds can be measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions can be 90 μM for Jak1, 30 μM for Jak2 and 3 μM for Jak3. Reactions can be carried out at room temperature for 1 hr and then stopped with 20 μL 45 mM EDTA, 300 nM SA-APC, 6 nM Eu-Py20 in assay buffer (Perkin Elmer, Boston, Mass.). Binding to the Europium labeled antibody can be for 40 minutes and HTRF signal can be measured on a Fusion plate reader (Perkin Elmer, Boston, Mass.). Compounds having an $IC_{50}$ of 10 μM or less for any of the above-mentioned JAK targets can be considered active.

Free Fraction Assay

The protein binding of a test compound can be determined by equilibrium dialysis using a Dianorm system from Harvard Apparatus (Holliston, Mass.). The dialysis can be performed at 37° C. for 2 hrs in human serum. The metabolites can be incubated at 3 μM, and Compound I at 3 and 10 μM. The compound concentrations in serum and buffer post-dialysis can be determined by LC/MS/MS analysis. Free fraction is defined as the ratio of the buffer versus serum concentration.

Intrinsic Clearance Assay

Intrinsic clearance can be determined by incubating 1 μM of test compound in human mixed gender liver microsomes (0.5 mg/mL protein) at 37° C. in the presence of 1 mM NADPH. The disappearance of the test compound can be monitored by LC/MS at 0, 5, 10, 20 and 30 min. The slope of decline in compound concentration can be used to calculate the human intrinsic clearance by employing standard methods reported in the literature.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:
1. A compound of Formula I:

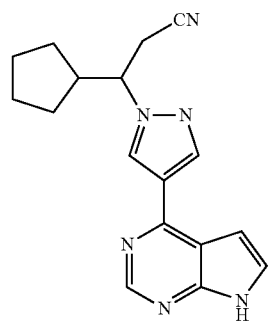

or a pharmaceutically acceptable salt thereof, wherein:
n C—H groups are each independently replaced with C—OH; or,
one $CH_2$ group is independently replaced with a C=O; and
n is 1, 2, 3, or 4;
provided that the compound is not selected from:
3-(4-(7H-pyrrolo[2,3-d]pyrimidin-4-yl)-1H-pyrazol-1-yl)-3-(3-hydroxycyclopentyl)propanenitrile;

3-(4-(7H-pyrrolo[2,3-d]pyrimidin-4-yl)-1H-pyrazol-1-yl)-3-(2-hydroxycyclopentyl)propanenitrile;
3-(4-(7H-pyrrolo[2,3-d]pyrimidin-4-yl)-1H-pyrazol-1-yl)-3-(3-oxocyclopentyl)propanenitrile;
and pharmaceutically acceptable salts thereof.

2. The compound of claim 1, or a pharmaceutically acceptable salt thereof,
wherein:
the carbon atom alpha to the cyano group is not replaced with a C—OH or C═O group; and
the carbon atom beta to the cyano group is not replaced with a C—OH group.

3. The compound of claim 1, or a pharmaceutically acceptable salt thereof, wherein n C—H groups are each independently replaced with C—OH.

4. The compound of claim 1, or a pharmaceutically acceptable salt thereof, wherein n is 1.

5. The compound of claim 1, or a pharmaceutically acceptable salt thereof, wherein n is 2.

6. The compound of claim 1, or a pharmaceutically acceptable salt thereof, wherein n is 3.

7. The compound of claim 1, or a pharmaceutically acceptable salt thereof, wherein n is 4.

8. The compound of claim 1, or a pharmaceutically acceptable salt thereof, wherein one CH$_2$ group is independently replaced with a C═O.

9. A compound of claim 1, selected from:
3-(4-(7H-pyrrolo[2,3-d]pyrimidin-4-yl)-1H-pyrazol-1-yl)-3-(1,2-dihydroxycyclopentyl)propanenitrile; and
3-(4-(7H-pyrrolo[2,3-d]pyrimidin-4-yl)-1H-pyrazol-1-yl)-3-(1-hydroxycyclopentyl)propanenitrile;
or a pharmaceutically acceptable salt of any of the aforementioned.

10. A compound of claim 1, selected from:
3-(4-(7H-pyrrolo[2,3-d]pyrimidin-4-yl)-1H-pyrazol-1-yl)-3-(1-hydroxycyclopentyl)propanenitrile;
3-(4-(7H-pyrrolo[2,3-d]pyrimidin-4-yl)-1H-pyrazol-1-yl)-3-cyclopentyl-3-hydroxypropanenitrile;
3-(4-(7H-pyrrolo[2,3-d]pyrimidin-4-yl)-1H-pyrazol-1-yl)-3-cyclopentyl-2-hydroxypropanenitrile;
3-cyclopentyl-3-(5-hydroxy-4-(7H-pyrrolo[2,3-d]pyrimidin-4-yl)-1H-pyrazol-1-yl)propanenitrile;
3-cyclopentyl-3-(3-hydroxy-4-(7H-pyrrolo[2,3-d]pyrimidin-4-yl)-1H-pyrazol-1-yl)propanenitrile;
3-cyclopentyl-3-(4-(5-hydroxy-7H-pyrrolo[2,3-d]pyrimidin-4-yl)-1H-pyrazol-1-yl)propanenitrile;
3-cyclopentyl-3-(4-(6-hydroxy-7H-pyrrolo[2,3-d]pyrimidin-4-yl)-1H-pyrazol-1-yl)propanenitrile;
3-cyclopentyl-3-(4-(2-hydroxy-7H-pyrrolo[2,3-d]pyrimidin-4-yl)-1H-pyrazol-1-yl)propanenitrile;
3-(4-(7H-pyrrolo[2,3-d]pyrimidin-4-yl)-1H-pyrazol-1-yl)-3-(1,2-dihydroxycyclopentyl)propanenitrile;
3-(4-(7H-pyrrolo[2,3-d]pyrimidin-4-yl)-1H-pyrazol-1-yl)-3-(1,3-dihydroxycyclopentyl)propanenitrile;
3-(4-(7H-pyrrolo[2,3-d]pyrimidin-4-yl)-1H-pyrazol-1-yl)-2-hydroxy-3-(1-hydroxycyclopentyl)propanenitrile;
3-(4-(7H-pyrrolo[2,3-d]pyrimidin-4-yl)-1H-pyrazol-1-yl)-3-hydroxy-3-(1-hydroxycyclopentyl)propanenitrile;
3-(3-hydroxy-4-(7H-pyrrolo[2,3-d]pyrimidin-4-yl)-1H-pyrazol-1-yl)-3-(1-hydroxycyclopentyl)propanenitrile;
3-(4-(2-hydroxy-7H-pyrrolo[2,3-d]pyrimidin-4-yl)-1H-pyrazol-1-yl)-3-(1-hydroxycyclopentyl)propanenitrile;
3-(4-(5-hydroxy-7H-pyrrolo[2,3-d]pyrimidin-4-yl)-1H-pyrazol-1-yl)-3-(1-hydroxycyclopentyl)propanenitrile;
3-(4-(6-hydroxy-7H-pyrrolo[2,3-d]pyrimidin-4-yl)-1H-pyrazol-1-yl)-3-(1-hydroxycyclopentyl)propanenitrile;
3-(5-hydroxy-4-(7H-pyrrolo[2,3-d]pyrimidin-4-yl)-1H-pyrazol-1-yl)-3-(1-hydroxycyclopentyl)propanenitrile;
3-(4-(7H-pyrrolo[2,3-d]pyrimidin-4-yl)-1H-pyrazol-1-yl)-2-hydroxy-3-(2-hydroxycyclopentyl)propanenitrile;
3-(4-(7H-pyrrolo[2,3-d]pyrimidin-4-yl)-1H-pyrazol-1-yl)-3-(2,3-dihydroxycyclopentyl)propanenitrile;
3-(4-(7H-pyrrolo[2,3-d]pyrimidin-4-yl)-1H-pyrazol-1-yl)-3-(2,4-dihydroxycyclopentyl)propanenitrile;
3-(4-(7H-pyrrolo[2,3-d]pyrimidin-4-yl)-1H-pyrazol-1-yl)-3-(2,5-dihydroxycyclopentyl)propanenitrile;
3-(4-(7H-pyrrolo[2,3-d]pyrimidin-4-yl)-1H-pyrazol-1-yl)-3-hydroxy-3-(2-hydroxycyclopentyl)propanenitrile;
3-(3-hydroxy-4-(7H-pyrrolo[2,3-d]pyrimidin-4-yl)-1H-pyrazol-1-yl)-3-(2-hydroxycyclopentyl)propanenitrile;
3-(4-(2-hydroxy-7H-pyrrolo[2,3-d]pyrimidin-4-yl)-1H-pyrazol-1-yl)-3-(2-hydroxycyclopentyl)propanenitrile;
3-(4-(5-hydroxy-7H-pyrrolo[2,3-d]pyrimidin-4-yl)-1H-pyrazol-1-yl)-3-(2-hydroxycyclopentyl)propanenitrile;
3-(4-(6-hydroxy-7H-pyrrolo[2,3-d]pyrimidin-4-yl)-1H-pyrazol-1-yl)-3-(2-hydroxycyclopentyl)propanenitrile;
3-(5-hydroxy-4-(7H-pyrrolo[2,3-d]pyrimidin-4-yl)-1H-pyrazol-1-yl)-3-(2-hydroxycyclopentyl)propanenitrile;
3-(4-(7H-pyrrolo[2,3-d]pyrimidin-4-yl)-1H-pyrazol-1-yl)-2-hydroxy-3-(3-hydroxycyclopentyl)propanenitrile;
3-(4-(7H-pyrrolo[2,3-d]pyrimidin-4-yl)-1H-pyrazol-1-yl)-3-(3,4-dihydroxycyclopentyl)propanenitrile;
3-(4-(7H-pyrrolo[2,3-d]pyrimidin-4-yl)-1H-pyrazol-1-yl)-3-hydroxy-3-(3-hydroxycyclopentyl)propanenitrile;
3-(5-hydroxy-4-(7H-pyrrolo[2,3-d]pyrimidin-4-yl)-1H-pyrazol-1-yl)-3-(3-hydroxycyclopentyl)propanenitrile;
3-(3-hydroxy-4-(7H-pyrrolo[2,3-d]pyrimidin-4-yl)-1H-pyrazol-1-yl)-3-(3-hydroxycyclopentyl)propanenitrile;
3-(4-(2-hydroxy-7H-pyrrolo[2,3-d]pyrimidin-4-yl)-1H-pyrazol-1-yl)-3-(3-hydroxycyclopentyl)propanenitrile;
3-(4-(5-hydroxy-7H-pyrrolo[2,3-d]pyrimidin-4-yl)-1H-pyrazol-1-yl)-3-(3-hydroxycyclopentyl)propanenitrile;
3-(4-(6-hydroxy-7H-pyrrolo[2,3-d]pyrimidin-4-yl)-1H-pyrazol-1-yl)-3-(3-hydroxycyclopentyl)propanenitrile;
3-(3-hydroxy-4-(7H-pyrrolo[2,3-d]pyrimidin-4-yl)-1H-pyrazol-1-yl)-3-(3-hydroxycyclopentyl)propanenitrile;
3-(4-(2-hydroxy-7H-pyrrolo[2,3-d]pyrimidin-4-yl)-1H-pyrazol-1-yl)-3-(3-hydroxycyclopentyl)propanenitrile;
3-(4-(5-hydroxy-7H-pyrrolo[2,3-d]pyrimidin-4-yl)-1H-pyrazol-1-yl)-3-(3-hydroxycyclopentyl)propanenitrile;
3-(4-(6-hydroxy-7H-pyrrolo[2,3-d]pyrimidin-4-yl)-1H-pyrazol-1-yl)-3-(3-hydroxycyclopentyl)propanenitrile;
3-(4-(7H-pyrrolo[2,3-d]pyrimidin-4-yl)-1H-pyrazol-1-yl)-3-cyclopentyl-2,3-dihydroxypropanenitrile;
3-cyclopentyl-3-hydroxy-3-(3-hydroxy-4-(7H-pyrrolo[2,3-d]pyrimidin-4-yl)-1H-pyrazol-1-yl)propanenitrile;
3-cyclopentyl-3-hydroxy-3-(4-(2-hydroxy-7H-pyrrolo[2,3-d]pyrimidin-4-yl)-1H-pyrazol-1-yl)propanenitrile;
3-cyclopentyl-3-hydroxy-3-(4-(5-hydroxy-7H-pyrrolo[2,3-d]pyrimidin-4-yl)-1H-pyrazol-1-yl)propanenitrile;
3-cyclopentyl-3-hydroxy-3-(4-(6-hydroxy-7H-pyrrolo[2,3-d]pyrimidin-4-yl)-1H-pyrazol-1-yl)propanenitrile;
3-cyclopentyl-3-hydroxy-3-(5-hydroxy-4-(7H-pyrrolo[2,3-d]pyrimidin-4-yl)-1H-pyrazol-1-yl)propanenitrile;
3-cyclopentyl-2-hydroxy-3-(3-hydroxy-4-(7H-pyrrolo[2,3-d]pyrimidin-4-yl)-1H-pyrazol-1-yl)propanenitrile;

3-cyclopentyl-2-hydroxy-3-(4-(2-hydroxy-7H-pyrrolo[2,3-d]pyrimidin-4-yl)-1H-pyrazol-1-yl)propanenitrile;
3-cyclopentyl-2-hydroxy-3-(4-(5-hydroxy-7H-pyrrolo[2,3-d]pyrimidin-4-yl)-1H-pyrazol-1-yl)propanenitrile;
3-cyclopentyl-2-hydroxy-3-(4-(6-hydroxy-7H-pyrrolo[2,3-d]pyrimidin-4-yl)-1H-pyrazol-1-yl)propanenitrile;
3-cyclopentyl-2-hydroxy-3-(5-hydroxy-4-(7H-pyrrolo[2,3-d]pyrimidin-4-yl)-1H-pyrazol-1-yl)propanenitrile;
3-cyclopentyl-3-(3,5-dihydroxy-4-(7H-pyrrolo[2,3-d]pyrimidin-4-yl)-1H-pyrazol-1-yl)propanenitrile;
3-cyclopentyl-3-(3-hydroxy-4-(2-hydroxy-7H-pyrrolo[2,3-d]pyrimidin-4-yl)-1H-pyrazol-1-yl)propanenitrile;
3-cyclopentyl-3-(3-hydroxy-4-(5-hydroxy-7H-pyrrolo[2,3-d]pyrimidin-4-yl)-1H-pyrazol-1-yl)propanenitrile;
3-cyclopentyl-3-(3-hydroxy-4-(6-hydroxy-7H-pyrrolo[2,3-d]pyrimidin-4-yl)-1H-pyrazol-1-yl)propanenitrile;
3-cyclopentyl-3-(4-(2,5-dihydroxy-7H-pyrrolo[2,3-d]pyrimidin-4-yl)-1H-pyrazol-1-yl)propanenitrile;
3-cyclopentyl-3-(4-(2,6-dihydroxy-7H-pyrrolo[2,3-d]pyrimidin-4-yl)-1H-pyrazol-1-yl)propanenitrile;
3-cyclopentyl-3-(4-(5,6-dihydroxy-7H-pyrrolo[2,3-d]pyrimidin-4-yl)-1H-pyrazol-1-yl)propanenitrile;
3-cyclopentyl-3-(5-hydroxy-4-(2-hydroxy-7H-pyrrolo[2,3-d]pyrimidin-4-yl)-1H-pyrazol-1-yl)propanenitrile;
3-cyclopentyl-3-(5-hydroxy-4-(5-hydroxy-7H-pyrrolo[2,3-d]pyrimidin-4-yl)-1H-pyrazol-1-yl)propanenitrile;
3-cyclopentyl-3-(5-hydroxy-4-(6-hydroxy-7H-pyrrolo[2,3-d]pyrimidin-4-yl)-1H-pyrazol-1-yl)propanenitrile;
2-(4-(7H-pyrrolo[2,3-d]pyrimidin-4-yl)-1H-pyrazol-1-yl)-2-cyclopentylacetyl cyanide; and
3-(4-(7H-pyrrolo[2,3-d]pyrimidin-4-yl)-1H-pyrazol-1-yl)-3-(2-oxocyclopentyl)propanenitrile;
or a pharmaceutically acceptable salt of any of the aforementioned.

11. A compound selected from:
3-cyclopentyl-3-(4-(2,6-dioxo-3,5,6,7-tetrahydro-2H-pyrrolo[2,3-d]pyrimidin-4-yl)-1H-pyrazol-1-yl)propanenitrile;
3-cyclopentyl-3-(4-(2-hydroxy-6-oxo-6,7-dihydro-5H-pyrrolo[2,3-d]pyrimidin-4-yl)-1H-pyrazol-1-yl)propanenitrile;
3-cyclopentyl-3-(4-(6-oxo-6,7-dihydro-5H-pyrrolo[2,3-d]pyrimidin-4-yl)-1H-pyrazol-1-yl)propanenitrile;
3-(3-hydroxycyclopentyl)-3-(4-(6-oxo-6,7-dihydro-5H-pyrrolo[2,3-d]pyrimidin-4-yl)-1H-pyrazol-1-yl)propanenitrile; and
3-cyclopentyl-3-(4-(5,6-dihydroxy-6,7-dihydro-5H-pyrrolo[2,3-d]pyrimidin-4-yl)-1H-pyrazol-1-yl)propanenitrile;
or a pharmaceutically acceptable salt of any of the aforementioned.

12. The compound of claim 1, or pharmaceutically acceptable salt thereof, which is substantially isolated.

13. A composition comprising a compound of claim 1, or a pharmaceutically acceptable salt thereof, and at least one pharmaceutically acceptable carrier.

14. The composition of claim 13, which is suitable for oral administration.

* * * * *